United States Patent
Corpstein et al.

(10) Patent No.: US 11,530,437 B2
(45) Date of Patent: Dec. 20, 2022

(54) MAGNETIC PARTICLES

(71) Applicant: Beckman Coulter, Inc., Brea, CA (US)

(72) Inventors: Jeffrey J. Corpstein, Noblesville, IN (US); Evan Farthing, Indianapolis, IN (US); Thomas G. Keen, Indianapolis, IN (US); Jianli Zhao, Cypress, CA (US); Asmita Patel, Carmel, IN (US); Yuandan Liu, Torrance, CA (US); Cuong N. Hoang, San Gabriel, CA (US); Emmet Welch, Folsom, CA (US)

(73) Assignee: Beckman Coulter, Isse., Brea, CA (US)

( * ) Notice: Subject to any disclaimer, the term of this patent is extended or adjusted under 35 U.S.C. 154(b) by 0 days.

(21) Appl. No.: 17/150,106

(22) Filed: Jan. 15, 2021

(65) Prior Publication Data

US 2021/0139953 A1 May 13, 2021

Related U.S. Application Data

(63) Continuation of application No. PCT/US2019/042628, filed on Jul. 19, 2019.

(60) Provisional application No. 62/700,658, filed on Jul. 19, 2018.

(51) Int. Cl.
| | |
|---|---|
| *H01F 1/00* | (2006.01) |
| *B82Y 25/00* | (2011.01) |
| *C12Q 1/6806* | (2018.01) |
| *H01F 1/36* | (2006.01) |
| *B82Y 30/00* | (2011.01) |
| *B82Y 40/00* | (2011.01) |

(52) U.S. Cl.
CPC .......... *C12Q 1/6806* (2013.01); *H01F 1/0054* (2013.01); *H01F 1/36* (2013.01); *B82Y 25/00* (2013.01); *B82Y 30/00* (2013.01); *B82Y 40/00* (2013.01); *C12Q 2563/143* (2013.01)

(58) Field of Classification Search
None
See application file for complete search history.

(56) References Cited

U.S. PATENT DOCUMENTS

| | | | |
|---|---|---|---|
| 4,965,007 A | 10/1990 | Yudelson | |
| 7,476,313 B2 | 1/2009 | Siddiqi | |
| 2006/0204442 A1* | 9/2006 | Tapolsky | A61P 35/00 424/9.32 |
| 2009/0289213 A1 | 11/2009 | Pipper et al. | |
| 2011/0274832 A1* | 11/2011 | Dai | H01F 1/0054 427/127 |
| 2013/0130035 A1 | 5/2013 | Contadini et al. | |
| 2013/0266509 A1* | 10/2013 | Pinol Lacambra | B01J 31/12 424/1.29 |
| 2014/0004583 A1* | 1/2014 | Corgie | C02F 3/342 435/156 |
| 2016/0211062 A1* | 7/2016 | Granger | B05D 1/007 |
| 2016/0281082 A1* | 9/2016 | Lellouche | C12N 15/113 |
| 2017/0216463 A1 | 8/2017 | Weissleder et al. | |

FOREIGN PATENT DOCUMENTS

| | | |
|---|---|---|
| CN | 103908945 A | 7/2014 |
| CN | 104258425 A | 1/2015 |
| CN | 112970076 A | 6/2021 |
| JP | 2021531461 A | 11/2021 |
| KR | 20160114476 | 10/2016 |
| KR | 101725240 B1 | 4/2017 |
| RU | 2336588 | 10/2008 |
| RU | 2417104 | 4/2011 |
| RU | 2687748 | 5/2019 |
| WO | WO-2020018919 A1 | 1/2020 |
| WO | WO-2020018919 A8 | 1/2020 |

OTHER PUBLICATIONS

Park et al, Langmuir, vol. 31, pp. 3537-3545, published Mar. 24, 2015.*
Bini et al, J. Magnetism and Mag. Mater., vol. 324, pp. 534-539, published online Aug. 26, 2011).*
"International Application Serial No. PCT/US2019/042628, International Search Report dated Oct. 29, 2019", 5 pgs.
"International Application Serial No. PCT/US2019/042628, Written Opinion dated Oct. 29, 2019", 5 pgs.
"Chinese Application Serial No. 201980060498.1, Voluntary Amendment filed Jun. 30, 2021", with English claims, 9.
"European Application Serial No. 19749121.0, Communication Pursuant to Article 94(3) EPC dated May 3, 2021", 3 pgs.
"International Application Serial No. PCT/US2019/042628, International Preliminary Report on Patentability dated Jan. 28, 2021", 7 pgs.
"Australian Application Serial No. 2019306640, First Examination Report dated Sep. 16, 2021", 3 pgs.
"European Application Serial No. 19749121.0, Response Filed Sep. 13, 2021 to Communication Pursuant to Article 94(3) EPC dated May 3, 2021", W/ Claims, 7 pgs.
"European Application Serial No. 19749121.0, Summons to Attend Oral Proceedings mailed Nov. 24, 2021", 4 pgs.
"Singapore Application Serial No. 11202100345R, Search Report and Written Opinion dated Feb. 11, 2022", 12 pgs.
"Thailand Application Serial No. 2101000223, Office Action dated Feb. 11, 2022", with Concise Statement of Relevance, 4 pages.

(Continued)

*Primary Examiner* — Robert T. Crow

(74) *Attorney, Agent, or Firm* — Schwegman Lundberg & Woessner, P.A.

(57) ABSTRACT

A magnetic particle is disclosed. The magnetic particle comprises a magnetic material having a maximum field strength in a range of from about 20 emu/g to about 250 emu/g and a remanence in a range of from about 0 emu/g to about 30 emu/g. The magnetic particle further comprises an outer surface containing a ligand. The ligand interacts with an analyte of interest in the sample solution.

24 Claims, 5 Drawing Sheets

(56) References Cited

OTHER PUBLICATIONS

"Russian Application Serial No. 2021103982, Office Action dated Dec. 21, 2021", with English translation, 17 pages.
"Russian Application Serial No. 2021103982, Response filed May 23, 2022 to Office Action dated Dec. 21, 2021", w/ English Claims, 12 pgs.
"Thailand Application Serial No. 2101000223, Response filed May 9, 2022 to Office Action dated Feb. 11, 2022", w/o English Claims, 9 pgs.

* cited by examiner

MAGNETIC PARTICLES

CROSS-REFERENCES TO RELATED APPLICATIONS

This application is a continuation of PCT Application No. PCT/US2019/042628, filed Jul. 19, 2019, which application claims the benefit of priority to U.S. Provisional Patent Application Ser. No. 62/700,658 entitled "MAGNETIC PARTICLES SUITABLE FOR MIXING IN RESPONSE TO A CHANGING MAGNETIC FIELD," filed Jul. 19, 2018, the disclosure of which is incorporated herein in its entirety by reference.

BACKGROUND

Magnetic particles (e.g., paramagnetic and superparamagnetic particles) are used for sample analysis and preparation in a variety of contexts, including chemical and biological assays and diagnostics. Such paramagnetic and superparamagnetic particles have also been used in microfluidic systems. Magnetic particle technology is a robust technology that provides for high performance (e.g., device sensitivity and accuracy) and also provides for easy automation of assay protocols. In some applications, the surface of a magnetic particles can be coated with a suitable ligand or receptor (e.g., antibodies, lectins, oligonucleotides, or other affinity groups), which can selectively bind a target substance or a group of analytes in a mixture. In some applications, the magnetic particles are used for mass transfer of components from one substrate to another substrate. One key element in magnetic particle separation and handling technology is efficient mixing to enhance the reaction rate between the target substances and the particle surfaces, the mass transfer from one substrate to another, or the transfer of an analyte from one medium to another.

Magnetic particles have also been used in sample plate applications. In magnetic sample plate systems, the sample plates include a plurality of fixed-field magnets arranged such that the magnets either protrude between the sample wells or allow the sample wells to be positioned within ring-shaped magnets. Magnetic particles within the sample wells can be agitated by placing a permanent magnet near the sample plate to promote mixing. Other types of automated mixing devices generally attempt to achieve mixing by mechanical agitation (e.g., by shaking the sample plate). After processing the samples, the magnets can be used to confine the particles to the side of the sample wells to allow for the removal of the sample fluid. However, the fixed-field magnets used in conventional magnetic sample plate applications are not capable of achieving robust mixing. For example, the magnetic particles generally tend to aggregate and cluster in discrete areas of the sample wells. The magnetic particles move with the liquid through small turbulent areas when using traditional mixing methods, thus making mixing inefficient. In addition, the plate itself must be moved between steps of the analysis, which requires significant automation.

BRIEF SUMMARY

Accordingly, a need exists to improve the overall speed and efficiency of sample mixing and separation using magnetic particles, including ultra-fast homogenous mixing of sample fluids. A need also exists for magnetic particles that have a high response to external magnetic fields as well as a low remanence. Furthermore, a need exists for the magnetic particles to remain suspended for a given time after mixing. A need also exists for a mixing method that mixes the magnetic particles through the liquid rather than with the liquid.

Examples of the invention address these and other challenges, individually and collectively.

A first aspect relates to a magnetic particle. The magnetic particle comprises a magnetic material having a maximum field strength in a range of from about 20 emu/g to about 250 emu/g and a remanence in a range of from about 0 emu/g to about 30 emu/g. The magnetic particle further comprises an outer surface containing a ligand. The ligand interacts with an analyte of interest in the sample solution.

Another aspect relates to a method of processing a sample. The method includes providing a magnetic particle having a ligand on a surface of the particle. The ligand selectively interacts with an analyte of interest in the sample. The magnetic particle has a maximum field strength in a range of from about 20 emu/g to about 250 emu/g and a remanence in a range of from about 0 emu/g to about 30 emu/g. The method further includes contacting a solution comprising the analyte of interest with the magnetic particle to allow the ligand to interact with the analyte of interest.

Another aspect relates to a method for processing a sample. First, a container comprising ferrimagnetic particles and a sample is provided. The container is subjected to a changing magnetic field, thereby moving the ferrimagnetic particles in the container and thereby processing the sample.

These and other examples are described in further detail below, with reference to the drawings.

DETAILED DESCRIPTION

Figure 1:
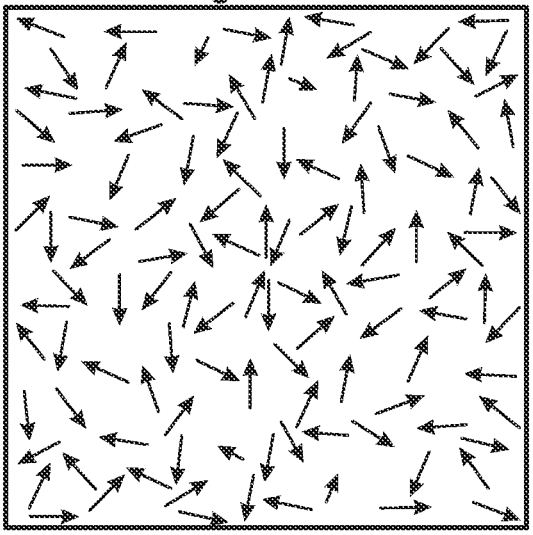
FIGS. 1-4 are cartoons of various types of magnetism according to the instant disclosure.

The present teachings generally relate to sample processing methods and systems for mixing, separating, filtering, or otherwise processing a sample (e.g., a fluid sample) by utilizing magnetic particles (e.g., ferrimagnetic particles) that are caused to move under the influence of a magnetic assembly disposed about the periphery of a container containing the sample. Although magnetic particles such as ferrimagnetic particles are described in conjunction with numerous embodiments, aspects, and examples in accordance with the instant disclosure it is also contemplated that magnetic particles such as ferromagnetic particles, paramagnetic particles, and superparamagnetic particles, or mixtures of various classes of magnetic particles can also be used. Therefore, any specific recitation of a ferrimagnetic particle can be equally applied to a ferromagnetic particle, paramagnetic particle, superparamagnetic particle, or mixtures thereof.

The present teachings provide multiple technological advantages, including increased magnetic field strength within the sample volume, thereby enabling improved mixing, improved mass transfer, and/or reduced power consumption relative to known magnetic particle mixing systems. The ferrimagnetic particles can exhibit a strong magnetic response relative to typical paramagnetic particles, thus allowing the ferrimagnetic particles to be more efficiently mixed through a sample using a magnetic assembly that generates changing magnetic fields. Additionally, the ferrimagnetic particles do not aggregate due to magnetically induced aggregation like typical ferromagnetic particles do.

Prior to discussing examples of the disclosure, some terms can be described in further detail.

As used herein, "ferrimagnetic particles" refers to particles comprising a ferrimagnetic material. Ferrimagnetic particles can respond to an external magnetic field (e.g., a changing magnetic field), but can demagnetize when the external magnetic field is removed. Thus, the ferrimagnetic particles are efficiently mixed through a sample by external magnetic fields as well as efficiently separated from a sample using a magnet or electromagnet, but can remain suspended without magnetically induced aggregation occurring.

The ferrimagnetic particles described herein are sufficiently responsive to magnetic fields such that they can be efficiently moved through a sample. In general, the range of the field intensity could be the same range as any electromagnet as long as it is able to move the particles. For example, the magnetic field has an intensity of between about 10 mT and about 100 mT, between about 20 mT and about 80 mT, and between about 30 mT and about 50 mT. In some examples, more powerful electromagnets can be used to mix less responsive microparticles. In some examples, the magnetic field can be focused into the sample as much as possible. Also, the electromagnets can be as close to the sample as possible since the strength of the magnetic field decreases as the square of the distance.

In some examples, the ferrimagnetic particle comprises a ferrite. A ferrite includes a ceramic material that comprise an oxide of iron in combination with inorganic compounds of metal, non-metal, or metalloid atoms. For example, a ferrite can comprise iron(III) oxide ($Fe_2O_3$) blended with one or more additional metallic elements, such as barium, manganese, nickel, zinc, titanium, or any other suitable metallic element. Other examples of ferrites include $Fe_2TiO_2$, $FeTiO_2$, $MnFe_2O_4$, $NiFe_2O_4$, $MgFe_2O_4$. further examples of ferrites include an iron core including a sulfide or an oxyhydroxide such as $Fe_7S_8$, $Fe_3S_4$, FeS, or FeOOH.

Magnetite ($Fe_3O_4$) is another example of a ferrimagnetic material useful in the examples described herein that is an example of a ferrite. Magnetite contains both $Fe^{2+}$ and $Fe^{3+}$ ions. In some cases, the electron spins of the $Fe^{2+}$ and $Fe^{3+}$ ions can be coupled in a crystalline structure such that the magnetite is ferrimagnetic, as described herein. However, in some examples, ferrimagnetic particles comprise any ferrimagnetic material (e.g., ferrite). According to some examples, the ferrimagnetic material (e.g., ferrite) may not be magnetite ($Fe_3O_4$), however in some examples, magnetite is a suitable ferrimagnetic material.

Ferrites can be categorized into two main families (hard ferrite and soft ferrites) based on their magnetic coercivity (e.g., the material's ability to withstand an external magnetic field without becoming demagnetized).

Hard ferrites have a high magnetic coercivity as well as a high remanence after magnetization. Hard ferrites can be used to make permanent magnets, as hard ferrites do not demagnetize easily in the absence of an external magnetic field, as they can have a high remanence. Examples of hard ferrites include strontium ferrite and barium ferrite.

Soft ferrites have a low magnetic coercivity. Soft ferrites also have a low remanence after magnetization. The magnetization of soft ferrites is easier to change than hard ferrites. Further, the magnetization of soft ferrites can easily reverse direction without dissipating large amounts of energy (e.g., via hysteresis losses). Soft ferrites can also have a high electrical resistivity, thus preventing the formation of eddy currents in the material, which is another source of energy loss.

Soft ferrites can include manganese-zinc (MnZn) ferrite and nickel-zinc (NiZn) ferrite. Thus, in some examples the ferrimagnetic particles comprise MnZn ferrite. In other examples, the ferrimagnetic particles comprise NiZn ferrite. Ferrimagnetic particles comprising MnZn ferrite and/or NiZn ferrite can become magnetized in the presence of an external magnetic field, and thus are able to be moved in the presence of the external magnetic field, but do not aggregate due to magnetically induced aggregation after the external magnetic field is removed, since they have a low remanence.

Some ferrites can be considered to be semi-hard ferrites. Semi-hard ferrites have properties that are between the properties of soft ferrites and the properties of hard ferrites. For example, cobalt ferrite ($CoFe_2O_4$) is a semi-hard ferrite, which can be magnetized in the presence of an external magnetic field (e.g., a changing magnetic field generated by a magnetic assembly), but does not have a high remanence after the external magnetic field is removed, such that the ferrimagnetic particles comprising a cobalt ferrite core do not aggregate due to magnetically induced aggregation.

A "magnetic domain" is a region within a magnetic material in which the net magnetization is in a uniform direction. Magnetic domains can occur in ferromagnetic and ferrimagnetic materials. A material can include many magnetic domains. The magnetization within a magnetic domain can point in a uniform direction. Each magnetic domain in a material can be oriented in a different direction. In the presence of an external magnetic field, the domains in a magnetic material can rotate so that each domain's magnetization aligns with the external magnetic field.

The term "remanence" refers to residual magnetism that a material retains after a magnetic field has been removed. Materials that have a high remanence after the magnetic field has been removed retain a large magnetic field strength, whereas materials that have a low remanence after the magnetic field has been removed have a small magnetic field strength or zero magnetic field strength. As used herein, the term "functional group-coated surface" refers to a surface which is coated with moieties which each have a free functional group which is bound to the ferrimagnetic particle; as a result, the surfaces of the ferrimagnetic particles are coated with the functional group containing moieties. The functional group acts as a bioaffinity absorbent for biological molecules in solution. In one example, the functional group is a carboxylic acid. A suitable moiety with a free carboxylic acid functional group is a succinic acid moiety in which one of the carboxylic acid groups is bonded to the amine of amino silanes through an amide bond and the second carboxylic acid is unbonded, resulting in a free carboxylic acid group attached or tethered to the surface of the ferrimagnetic particle. Other suitable functional groups that can used for coating the surface of the ferrimagnetic particles include, but are not limited to thiol groups, streptavidin, avidine, neutravidin, captavidin, amine groups, hydroxyl groups, tosyl groups, epoxy groups, alkyl groups, vinyl groups, or aryl groups. According to further examples the surface can be coated with a biomolecule, such as an enzyme, protein, deoxyribonucleic acid (DNA), ribonucleic acid (RNA), immunoglobulin G, or an antibody (e.g., a monoclonal antibody).

A sample used in the present disclosure can be a fluid sample and can be, for example, a biological sample or a chemical sample. As used herein, "biological samples" can comprise biological fluids and may include, but are not limited to, blood, plasma, serum, or other bodily fluids or excretions, such as but not limited to saliva, urine, cerebrospinal fluid, lacrimal fluid, perspiration, gastrointestinal fluid, amniotic fluid, mucosal fluid, pleural fluid, sebaceous oil, exhaled breath, and the like. Chemical samples can include any suitable types of samples comprising chemicals to be detected, including water samples.

Appropriate biological samples may also include lysates prepared from cells obtained from either mammalian tissue, cell culture, or body fluids, nucleic acid samples eluted from agarose or polyacrylamide gels, solutions containing multiple species of DNA molecules resulting either from a polymerase chain reaction (PCR) amplification or from a DNA size selection procedure and solutions resulting from a post-sequencing reaction. Suitable samples can be mixtures of biomolecules (e.g. proteins, polysaccharides, lipids, low molecular weight enzyme inhibitors, oligonucleotides, primers, templates) and other substances such as agarose, polyacrylamide, trace metals and organic solvents, from which the target nucleic acid molecule can be isolated.

The term "analyte" refers to a substance whose presence, absence, or concentration is to be determined according to examples of the present disclosure. Examples of analytes may include, but are not limited to biological molecules, such as hormones (such as thyroid hormones, estradiol, testosterone, progesterone, estrogen), metabolites (such as glucose or ethanol), proteins, lipids, carbohydrates and sugars, steroids (such as Vitamin D), peptides (such as procalcitonin), and nucleic acids. The analyte can also be, cells, cell components (such as cell membranes), spores, biomarkers (pharmaceuticals such as antibiotics, benzodiazepine), drugs (such as immunosuppressant drugs, narcotics, opioids, etc.), molecules with a regulatory effect in enzymatic processes such as promoters, activators, inhibitors, or cofactors, microorganisms, such as viruses (including EBV, HPV, HIV, HCV, HBV, Influenza, Norovirus, Rotavirus, Adenovirus etc.), bacteria (*H. pylori, Streptococcus*, MRSA, *C. diff., Ligionella*, etc.), fungi, parasites (plasmodium, etc.). Examples of the disclosure can also allow for the simultaneous analysis of multiple analytes in the same class or different classes (e.g. simultaneous analysis of metabolites and proteins). In examples of the disclosure, the analysis of a particular analyte such as a biomarker may indicate that a particular condition (e.g., disease) is associated with a sample that contains the analyte.

As used herein, the term "isolated" is intended to mean that the material in question exists in a physical milieu distinct from that in which it occurs in nature and/or has been completely or partially separated or purified from other non-target molecules.

As used herein, the terms "selective" and "selectively" refer to the ability to isolate a particular biological molecule species such as a DNA molecule or molecules, on the basis of particular property, such as molecular size, from a combination which includes or is a mixture of species of molecules, such as a host cell lysate and other host cell components. In some examples, the selective isolation of a particular species is accomplished through the use of an appropriate precipitating reagent (e.g., polyalkylene glycol salt) to result in the precipitation and facilitated adsorption of a particular DNA species (e.g., characterized on the basis of size) to the surfaces of ferrimagnetic particles of the disclosure.

The term "analyzer" includes any suitable instrument that is capable of analyzing a sample such as a biological sample. Examples of analyzers include mass spectrometers, immunoanalyzers, hematology analyzers, microbiology analyzers, and/or molecular biology analyzers.

I. MAGNETIC PARTICLES

In accordance with various aspects of the present teachings, magnetic particles, for example such as ferrimagnetic particles can be mixed throughout a container. The ferrimagnetic particles are manipulated (e.g., moved) by a changing magnetic field generated by a magnetic assembly.

The ferrimagnetic particles of the disclosure, have a high response to magnetic fields, such that the ferrimagnetic particles are easily mixed into a sample when in the presence of an external changing magnetic field. The ferrimagnetic particles can also have a low residual magnetism, such that the ferrimagnetic particles are not magnetically attracted to one another when an external changing magnetic field is removed. As a result, the ferrimagnetic particles can remain suspended without magnetically induced aggregation occurring after mixing and thus do not inhibit binding or elution.

Further, the ferrimagnetic particles should remain suspended in the sample for a suitable time after mixing. One of skill will recognize that a number properties of the ferrimagnetic particles will affect this property. For example, the density, as well as the remanence (e.g., residual magnetism), of the ferrimagnetic particles can influence the length of time of suspension in the sample after the changing magnetic field is removed. In some examples it is desirable to separate the ferrimagnetic particles from the sample. In these examples, the ferrimagnetic particles can be magnetically separated from the container using a collection component, such as a magnet or an electromagnet, as described herein.

The ferrimagnetic particles can be a variety of shapes, which can be regular or irregular; In some examples, the shape maximizes the surface areas of the particles. For example, the ferrimagnetic particles can be spherical, bar shaped, elliptical, or any other suitable shape. The ferrimagnetic particles can be a variety of densities, which can be determined by the composition of the core. In some examples, the density of the ferrimagnetic particles can be adjusted with a coating, as described herein.

In some examples, the ferrimagnetic particles have sufficient surface area to permit efficient binding of a target analyte and are further characterized by having surfaces which are capable of reversibly or irreversibly binding the target analyte (e.g., biological molecules). In some examples, a surface area of the ferrimagnetic particles can be in a range of from about 0.1 $m^2/g$ to about 500 $m^2/g$, about 50 $m^2/g$ to about 200 $m^2/g$, or about 150 $m^2/g$ to about 175 $m^2/g$.

Suitable ferrimagnetic particles can be of a size that their separation from solution is not difficult, for example by magnetic means or by filtration. In addition, ferrimagnetic particles should not be so large that their surface area is minimized or that they are not suitable for nanoscale to microscale manipulation Suitable sizes range from about 1 nm mean diameter to about 1 mm mean diameter, about 5 nm to about 50 μm, or between about 100 nm and about 100 μm. A suitable is between about 1 µm and about 10 µm. For example, in some examples, the ferrimagnetic particles can be nanoparticles (e.g., particles having a mean diameter less than 1 µm, but greater than 1 nm). In other examples, the ferrimagnetic particles can be microparticles (e.g., particles having a mean diameter greater than 1 µm, but less than 100 µm). In general, larger ferrimagnetic particles (that is about 1 mm in size) are useful in cellular fractionation, tissue digestion, liquid mixing, and the like.

The ferrimagnetic particles can be substantially solid or can have some degree of porosity. Where the ferrimagnetic particles do include some degree of porosity, a pore size of the individual pores can be in a range of from about 5 Å to about 1000 Å, about 50 Å to about 500 Å. At least a plurality of the pores can be through pores (e.g., extending fully between opposed surfaces). The pore sizes or total porosity of the ferrimagnetic particles can be determined according to many suitable methods. For example, the bulk volume of an ideal (e.g., non-porous) ferrimagnetic particle can be determined and then the volume of the actual porous skeletal material can be determined. The porosity is then calculated by subtracting the volume of the actual porous skeletal material from the ideal ferrimagnetic particle. The porosity of the ferrimagnetic particle or individual pore size can also be determined through optical measurements using a microscope and processing the images to measure the individual pores.

The ferrimagnetic particles described herein can include several different materials. To the extent that mixtures of materials are present, the total magnetic content of the ferrimagnetic particles can constitute at least 50 wt % of the ferrimagnetic particle, at least 70 wt % of the ferrimagnetic particle, or even 100 wt % of the ferrimagnetic particle. The ferrimagnetic particles can include any of those described herein. The non-magnetic material constituting the balance of the ferrimagnetic particles can include any of the coating materials described herein, for example. Non-magnetic material can be used as a coating to encapsulate the magnetic portion of the ferrimagnetic particle, they can also be used as a functional component to interact with and bind an analyte of interest. Non-magnetic material can also act a as filler component.

A. Magnetism

Those of skill recognize a number of different types of magnetism including paramagnetism, superparamagnetism, ferromagnetism, antiferromagnetism, and ferrimagnetism. FIG. 1 shows examples of various different types of magnetism. The arrows in FIGS. 1-4 indicate magnetic moments of particles, for example, electrons, in different materials, however, it is understood that atoms and molecules can also create magnetic moments. Each arrow represents the magnetic strength (by length of the arrow) and orientation of the magnetic moment (by orientation of the arrow).

Paramagnetism occurs in the presence of unpaired electrons in a material. FIG. 1 shows magnetic moments in a paramagnetic material in the absence of an external magnetic field. The magnetic moments are not aligned and can point in random directions due to thermal motion. The material has a net magnetism of zero since the magnetic moments point in random directions, thus cancelling one another out. In the presence of an external magnetic field, the magnetic moments align parallel to the external magnetic field. The paramagnetic material then forms an induced magnetic field in the direction of the external magnetic field, causing a net attraction. Paramagnetic materials only exhibit magnetism in the presence of an external magnetic field. Paramagnetic materials can be weakly magnetically responsive. Examples of paramagnetic materials include aluminum, oxygen, titanium, and iron oxide (FeO).

Figure 2:
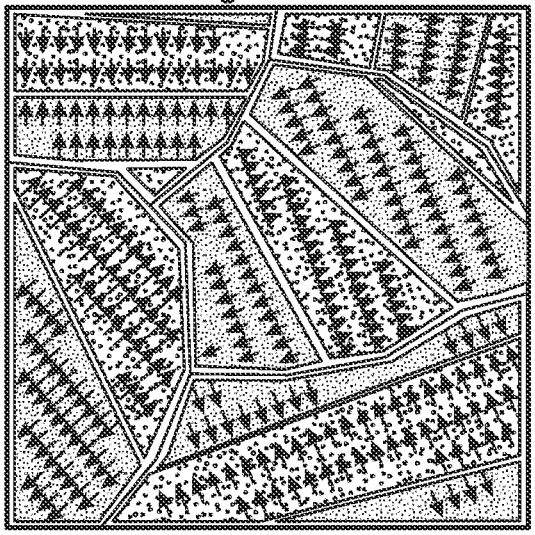

Materials that are ferromagnetic can be magnetized by an external magnetic field, e.g., the magnetic moments of the material align in the same direction, and remain magnetized after the external magnetic field is removed. FIG. 2 shows a number of aligned magnetic moments in a ferromagnetic material in the absence of an external magnetic field. A ferromagnetic material can form an induced magnetic field in the direction of the aligned magnetic moments.

Ferromagnetism is a property not just of the chemical make-up of a material, but also of the material's crystalline structure and microstructure. For example, there are ferromagnetic metal alloys that comprise elements that are not ferromagnetic. A ferromagnetic material has a high susceptibility to an external magnetic field and tends to retain a magnetic field after the external magnetic field is removed. Particles comprising a ferromagnetic material can undergo magnetically induced aggregation since they retain a magnetic field. Thus, after a magnetic mixer mixes ferromagnetic particles throughout a sample, the ferromagnetic particles can remain magnetized and clump together. Examples of ferromagnetic materials include iron, nickel, and cobalt.

Figure 4:
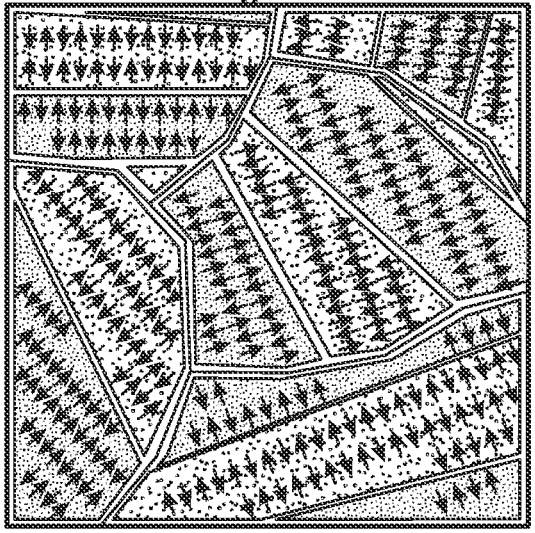

A ferrimagnetic material can have multiple populations of atoms with opposing magnetic moments. FIG. 4 shows magnetic moments of two different populations of atoms that are anti-aligned and unequal. The magnetic moments of one population can be stronger than the magnetic moments of another population, thus causing a net magnetism. The crystal structure of a ferrimagnetic material comprise magnetic sublattices of magnetic moments, wherein the magnetic moments of the two sublattices are anti-aligned and not equal. The opposing magnetic moments are unequal and a spontaneous magnetization remains. Ferrimagnetic materials can also have a high electrical resistivity. When the external magnetic field is removed from a ferrimagnetic material, the ferrimagnetic material can remain magnetized or can become unmagnetized depending upon the specific ferrimagnetic material. An example of a ferrimagnetic material is a ferrite.

Figure 3:
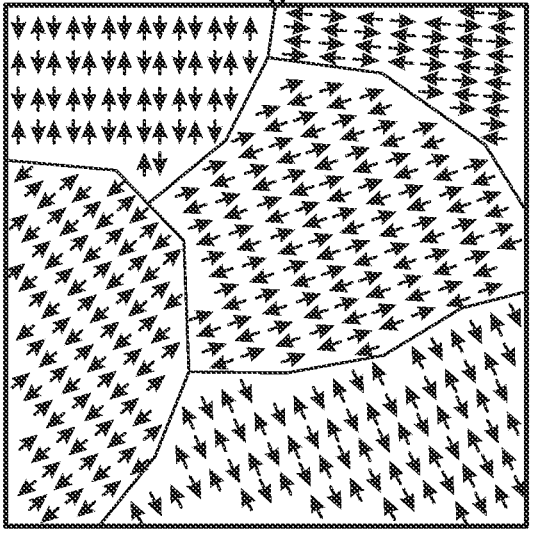

FIG. 3 shows magnetic moments in an antiferromagnetic material. There, the two different populations are anti-aligned and equal. One population of magnetic moments points in one direction, while the second population of magnetic moments points in the opposite direction. The strength of these two populations of magnetic moments is equal, thus, in the presence of an external magnetic field, an antiferromagnetic particle will not create an induced magnetic field.

Superparamagnetism is a fifth type of magnetic behavior, in which nanoparticles, for example smaller than 50 nm in size, made of a ferromagnetic or ferrimagnetic material, are small enough to contain a single magnetic domain. Superparamagnetic materials can exhibit paramagnetic-like behavior outside of a magnetic field, but can be more magnetically responsive than paramagnetic materials in the presence of an external magnetic field.

According to various examples, the magnetic strength of the ferrimagnetic particles can be greater than or equal to about 20 emu/g, about 25 emu/g, about 30 emu/g, about 35 emu/g, about 40 emu/g, about 45 emu/g, about 50 emu/g, about 75 emu/g, about 100 emu/g, about 150 emu/g, about 175 emu/g, about 200 emu/g, about 225 emu/g, about 250 emu/g, in a range of from about 20 emu/g to about 250 emu/g, or about 35 emu/g to about 100 emu/g. This value can be considered to be the maximum field strength of the particle, which is a measure of the magnetic strength generated by the particle upon exposure to a magnetic field. In combination with the magnetic strength of the ferrimagnetic particles, the permeability of the ferrimagnetic particle should be sufficient to generate an induced magnetic field greater than or equal to about 10 emu/g, 15 emu/g, 20 emu/g, about 25 emu/g, about 30 emu/g, about 35 emu/g, about 40 emu/g, about 45 emu/g, about 50 emu/g, about 75 emu/g, about 100 emu/g, about 150 emu/g, about 175 emu/g, about 200 emu/g, about 225 emu/g, about 250 emu/g, in a range of from about 10 emu/g to about 250 emu/g, or about 35 emu/g to about 100 emu/g. The magnetic field to which the ferrimagnetic particles are exposed, can have a strength of about 700 Oersted to about 800 Oersted, about 725 Oersted to about 775 Oersted, less than, equal to, or greater than about 700 Oersted, 725, 750, 775, or about 800 Oersted.

According to various examples, the remanence of the ferrimagnetic materials can be in a range of from about 0 emu/g to about 30 emu/g, about 0 emu/g to about 10 emu/g, about 1 emu/g to about 8 emu/g, about 3 emu/g to about 5 emu/g, less than, equal to, or greater than about 0 emu/g, 1, 2, 3, 4, 5, 6, 7, 8, 9, 10, 11, 12, 13, 14, 15, 16, 17, 18, 19, 20, 21, 22, 23, 24, 25, 26, 27, 28, 29, or about 30 emu/g.

The magnetic components of the particles can be magnetic nanoparticles, magnetic sub-micrometer particles, or magnetic micrometer particles. The ferrimagnetic particles described herein can have many different structures. For example, the ferrimagnetic particles can be magnetic nanoparticles incorporated in polymer matrix or silica matrix, magnetic beads encapsulated in silica shell or polymer shell, magnetic nanoparticles or magnetic beads functionalized with organic ligands, bare magnetic nanoparticles or beads. In examples where the ferrimagnetic particles are core-shell particles, the shell can include a coating as described herein.

B. Coating

The ferrimagnetic particles of the disclosure can comprise a ferrimagnetic core, surrounded by a coating. In an example, the ferrimagnetic particles are coated with one or more layers of a non-magnetic material. The use of coated ferrimagnetic particles, having no exposed iron, on their surfaces, can eliminate the possibility of iron interfering with certain downstream manipulations of the sample. The coating can be, for example, a polymer layer, or a silica layer.

Example polymer layers can include polyethylene, polystyrene, poly methyl methacrylate, polyvinyl alcohol, or any other suitable polymer. Example silica layers can include silicon dioxide, borosilicate, soda lime, barium titanate, and other types of glass. The polymer or silica layer can be for adjusting the density of the ferrimagnetic particles. For example, the polymer or silica layer can adjust the density of the ferrimagnetic particles to be close to the density of the sample, for example, an aqueous sample (e.g., approximately 1 $g/cm^3$).

In other examples, other types of coating can include metal plating such as aluminum, gold, zinc oxide, or any of the other coatings mentioned herein, etc. Furthermore, any of the coatings described herein can have a fluorescent or colored dye included.

The coating can also comprise a ligand such as capture reagent or a functional group, including those mentioned herein, for selectively or non-selectively binding target analytes. The functional group can be for adsorbing biomolecules, such as nucleic acids, which can non-sequence-specifically and reversibly bind to the functional group coating the ferrimagnetic particles. The polynucleotides can be DNA, RNA, or polyamide nucleic acids (PNAs). In an example, the functional group is a carboxyl group. Various coatings comprising functional groups suitable for these purposes are described in U.S. Pat. Nos. 5,705,628, 5,898,071, and 6,534,262, the teachings of which are hereby incorporated by reference into this application in their entirety. Any of the coatings described herein can be functionalized with surface chemicals as described herein, for example, with carbolic acid, streptavidin, amine, hydrazide, silanol, azide. And those can be further functionalized with biological molecules such as antibodies, enzymes, DNA or RNA fragments, catalysts, etc.

In some examples, the coating can comprise a capture reagent. The capture reagent can be for capturing an analyte in a sample. The surface of the ferrimagnetic particles can be coated with a capture reagent that is a suitable ligand or receptor (e.g., antibodies, lectins, oligonucleotides, other affinity groups, or any of the other capture reagents mentioned herein), which can selectively bind a target analyte or a group of analytes in a mixture. In some examples, the capture reagent can be an antibody.

Those of skill will recognize that any number of capture reagents can be used for this purpose, e.g. aptamers, nanoparticles, binding proteins, and the like. The capture reagent can be designed to capture a specific analyte or a specific panel of analytes, e.g., drug panel or endocrine panel, etc.

Alternatively, the ligand can include an enzyme. In some embodiments the enzyme can be linked to the coating in order to selectively interact with a substrate of that enzyme. Upon interacting with the substrate, the enzyme can function to degrade or digest the substrate. This can lead to generation of a substance of interest through enzyme's action or to remove a substrate from a sample. According to various embodiments, the enzyme can be trypsin.

While only a single layer of coating is described it is understood that some examples can include multiple layers of coatings. For example, some examples can include a base metal coating with a polymer coating or functional group disposed thereon. In some examples, a layer of coating can function to sufficiently hold an external coating to the ferrimagnetic particle.

C. Manufacture

The ferrimagnetic particles can be manufactured using any suitable method of manufacturing nanoscale to microscale magnetic particles. As an example, U.S. Pat. No. 5,648,124 discloses a process for preparing magnetically responsive microparticles, and is hereby incorporated by reference herein in its entirety. The ferrimagnetic particles can be manufactured using any suitable ferrimagnetic material, as described herein.

For example, a ferrimagnetic particle can be manufactured by first adding ferrimagnetic nanoparticles to a chemical bath. The nanoparticles can be encapsulated in an inorganic silica matrix, thus producing a microparticle that contains many ferrimagnetic particles. Sonication can then be used to help produce these particles in a monodispersed fashion. Although a silica matrix is mentioned above, it is also possible for individual ferrimagnetic nanoparticles or microparticles to be encapsulated in other inorganic or organic materials. For example, the ferrimagnetic nanoparticles can be encapsulated in $SiO_2$, $TiO_2$, $ZnO_2$, $Al_2O_3$, $CeO_2$, or any suitable ceramic material. As a further example, the ferrimagnetic nanoparticles can be encapsulated in an organic material such as polyacrylic acid (PAA), poly(methyl acrylate)(PMA), polystyrene (PS), divinylbenzene (DVB), polyvinylpyrrolidone (PVP), or polyvinyl alcohol (PVA).

In another example, a ferromagnetic material can be used to manufacture ferrimagnetic particles. The magnetic properties can be altered by changing the structure of the ferromagnetic material. Hematite ($Fe_2O_3$) is naturally ferromagnetic when allowed to crystalize in its pure form. However, if impurities like nickel and zinc are added, then the nickel and zinc can take the place of some of the iron in the crystalline structure, thus turning the naturally ferromagnetic material into a ferrimagnetic particle. Or, in a different example, ferromagnetic hematite can be ground down to less than 50 nm in size such that each particle contains a single magnetic domain. In this form, the particle can be a superparamagnetic particle. An exemplary ferrimagnetic particle can be made from ferrimagnetic magnetite nanoparticles 50-100 nm in size joined together in silica or polymer. These nanoparticles are too large to be superparamagnetic.

II. SYSTEM

The present teachings generally relate to sample processing methods and systems for mixing, separating, filtering, or otherwise processing a sample (e.g., a fluid sample) in a container by utilizing ferrimagnetic particles of the disclosure that are caused to move under the influence of a magnetic assembly disposed about the container.

Thus. a sample processing system of the disclosure can comprise a container, ferrimagnetic particles, a magnetic assembly disposed about the periphery of the container, and a control component coupled to the magnetic assembly. The magnetic assembly can comprise at least one magnetic structure, each magnetic structure comprising a plurality of electromagnets disposed about the periphery of the container. Each electromagnet being individually controlled by the control component to generate a desired magnetic field within the container effective to influence the ferrimagnetic particles, for example, in accordance with a sample processing method comprising various steps. In some examples, the magnetic assembly can comprise a plurality of magnetic structures. The magnetic structures can be arranged in horizontal or substantially horizontal layers. In other examples, the magnetic structures can be arranged in vertical or substantially vertical layers.

In yet other examples, there can be a magnetically-permeable field shorting plate or structure below, above, and/or between the magnetic structures. The magnetically-permeable field shorting plate drastically reduces power consumption by concentrating the magnetic field in one particular location instead of two.

In some examples, the sample processing system can further comprise a magnet or an electromagnet capable of collecting the ferrimagnetic particles in the container, thereby allowing the ferrimagnetic particles to be separated from the sample disposed in the container.

It will be appreciated by those skilled in the art that the container, magnetic assembly, and the control component can be configured in any suitable manner to generate changing magnetic fields (e.g., oscillating magnetic fields, rotating magnetic fields) in the container. PCT Application No. PCT/IB2016/057189 to Arnold et al. discloses electromagnetic assemblies for processing fluids suitable for use in the present disclosure, and is hereby incorporated by reference herein in its entirety.

A. Container

Figure 5:
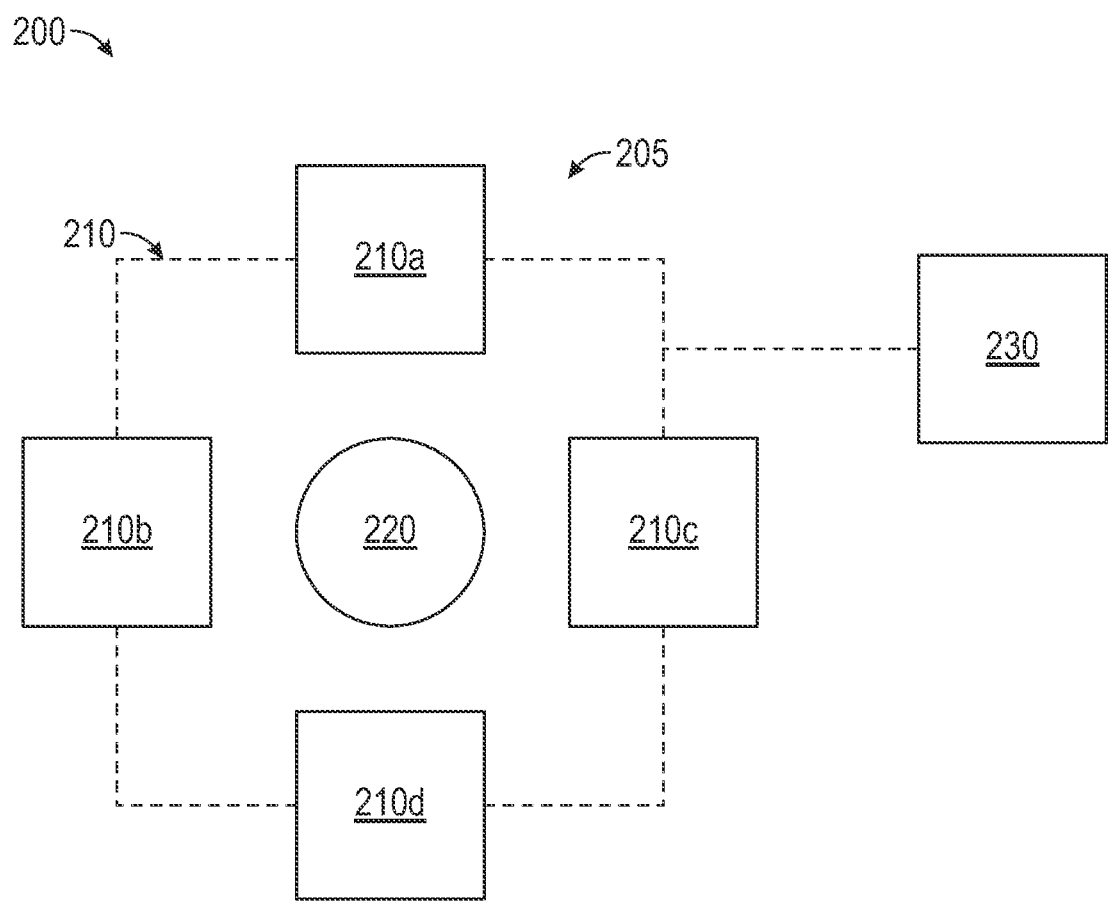
FIG. 5 is a block diagram of a sample processing system according to the instant disclosure.

The sample processing system can comprise a container containing a sample for processing. The container can generally be any type of container configured to hold a sample (e.g., a fluid sample), such as a sample well, a vial, a fluid reservoir, or the like, defining a fluid-containing chamber therein. As shown in FIG. 5, the sample processing system 200 can comprise a container 220. The exemplary container 220 can extend from an open, upper end (open to the ambient atmosphere) to a lower, closed end such that the sample within the container 220 can be loaded into the open, upper end and/or removed therefrom by one or more liquid loading/collection devices (not shown). It will be appreciated by those skilled in the art that the container can include a removable cap that can be coupled to the open, upper end (e.g., an Eppendorf tube) during various processing steps, for example, to prevent the escape of fluid, contamination, and/or evaporation. Illustrative liquid loading/collection devices can include, without limitation, manual sample loading devices (e.g., pipette), multi-channel pipette devices, acoustic liquid handling devices, and/or an autosampler, all by way of non-limiting example.

Sample processing systems, described herein, can be configured to process samples at the micro-scale or macro-scale (including large-volume formats). In general, the macro-scale involves fluid volumes in the milliliter range, while micro-scale fluid processing involves fluid volumes below the milliliter range, such as microliters, nanoliters, or picoliters. Large-volume formats can involve the processing of fluid volumes greater than 1 mL. For example, sample processing systems in accordance with various aspects of the present teaching can be capable of processing a fluid volume of about 10 µL to about 1 mL and even greater, including for example, about 1.5 mL, about 2 mL, about 5 mL, about 10 mL, or greater. However, it will be appreciated in light of the present teachings that the sample processing systems can process any fluid volume capable of operating as described herein. In another example, the container can be capable of processing a fluid volume of about 10 µL to 500 µL.

In accordance with various aspects of the present teachings, systems and methods described herein can utilize containers that can be filled or partially-filled with various volumes of the sample, thereby allowing for the reduction or expansion of the sample volume to be processed, depending for example on the availability or expense of the sample and/or on the requirements of a particular assay. In some aspects, samples to be processed (and the reagents utilized to process the same) can be directly added to the open container (e.g., via an auto-sampler or pipette inserted through the open end of the container) and can likewise be directly removed therefrom (e.g., via a collection component) following the processing, for example.

By way of another example, the container can comprise a chamber having continuous fluid flow. In some aspects, for example, the container can comprise an open port probe, the open port probe comprising a tubular member, an inlet for the inflow of a sample and an outlet for the outflow of the sample and a tip end open to the atmosphere and configured such that the inflow and outflow of the sample are directed to the tip end to maintain a steady state level of sample. In related aspects, the open port probe can be configured to receive a substrate having an analyte in at least a portion of its surface to the sample to cause transfer of at least a portion of the analyte from the substrate surface to the sample. By way of non-limiting example, the substrate can be a solid phase microextraction (SPME) fiber.

As a further example, the open port probe can comprise a tube having an open ended tip that is configured to both introduce and extract sample on a continuous basis providing a steady state level of sample at a tip end. In this particular example, the open port probe can comprise a first cylindrical member disposed within a second cylindrical member arranged in a co-axial arrangement. The sample travels towards the tip end through an annular space between the two cylindrical members and then travels away from the tip end through the inner cylinder. As should be appreciated, if no inflow or outflow of fluid is present, the sample level will remain steady and in many respects, the open port probe will operate in a similar manner to the other containers described previously, such as a vial. The open port probe can be used to extract analytes from a substrate surface that comes into contact with the sample at the tip end. In several examples, ferrimagnetic particles can be introduced into the sample at the tip end of the open port probe and in combination with the sample processing systems and magnetic assemblies and/or structures, comprising electromagnets herein described, the ferrimagnetic particles can be influenced to resist the outflow of sample from the tip end and remain in the vicinity of the tip end by virtue of the presence of the magnetic fields. In addition, the magnetic assemblies and/or structures cause the ferrimagnetic particles to spin, or travel back and forth in x-, y-, and z-directions as confined by the presence of the magnetic fields. While the electromagnets can be chosen to be sufficiently strong to prevent any escape of ferrimagnetic particles from the tip surface, a downstream permanent magnetic, or an electromagnet, (not shown) can also be used to capture ferrimagnetic particles, thereby preventing any downstream analysis from contamination.

While cylindrical members have been described above in describing the tube, it should be appreciated that other shapes with varying cross-sectional shapes can also be utilized include triangular, square, rectangular or any other multi-sided shape. The magnetic assemblies and/or magnetic structures that comprise electromagnets can be placed outside of the metal tube or can be part of the metal tube itself and directly integral to metal at or near the tip.

B. Magnetic Assembly

While the systems, devices, and methods described herein can be used in conjunction with many different sample processing systems, an exemplary sample processing system 200 is illustrated schematically in FIG. 5. It should be understood that the sample processing system 200 represents only one possible sample processing system for use in accordance with examples of the systems, devices, and methods described herein, and sample processing systems and/or components thereof having other configurations and operational characteristics can all be used in accordance with the systems, devices, and methods described herein as well. As shown in FIG. 5, the exemplary sample processing system 200 includes a magnetic assembly 205 comprising at least one magnetic structure 210. The magnetic structure 210 comprising a plurality of electromagnets 210*a-d*. As discussed in detail below, the magnetic assembly 205 is configured to generate a changing magnetic field or magnetic force within the container 220 and can comprise at least one magnetic structure 210 that can be disposed relative to the container 220 so as to generate a magnetic field therein. In some examples, the magnetic assembly 205 can be configured to generate a static magnetic field, thereby collecting the ferrimagnetic particles. Each magnetic structure 210 can comprise a plurality of electromagnets 210*a-d*, each of the plurality of electromagnets 210*a-d* having an electrically-conductive coil disposed about a centerline that extends toward a center axis of the magnetic structure 210.

As noted above, each magnetic structure 210 of the magnetic assembly 205 can include a plurality of electromagnets 210*a-d*. Although four electromagnets 210*a-d* are associated with the magnetic structure 210, for example, it will be appreciated that the present teachings are not so limited as any number of electromagnets capable of operating according to various aspects of the applicant's teachings can be used. For example, a magnetic structure 210 can include 2 electromagnets, 3 electromagnets, 4 electromagnets, 5 electromagnets, 6 electromagnets, 7 electromagnets, 8 electromagnets, 9 electromagnets, 10 electromagnets, or more. The electromagnets can include any electromagnet known to those having skill in the art, including, for example, a ferromagnetic-core solenoid. The electromagnets can have various shapes, including square, rectangular, round, elliptical, or any other shape capable of operating according to various aspects of the applicant's teachings. Additionally, in some aspects, magnetic lenses can be utilized so as to modify (e.g., re-shape) the magnetic field generated by the electromagnets within the container.

In accordance with various aspects of the present teachings, the magnetic structure 210 can be incorporated into various sample processing systems 200 and fluid handling devices. A sample processing system can include, for example, one or a plurality of magnetic structures 210 arranged in horizontal or substantially horizontal layers. Additionally, or alternatively, in some examples, the electromagnets of the various magnetic structures 210 (e.g., of the different vertically-spaced layers) can be selectively energized so as to process different sample volumes and/or to affect a characteristic of a magnetic field generated by the magnetic assembly 205.

For example, the magnetic assembly 205 can include a plurality of magnetic structures. Each of the magnetic structures comprises a horizontal or substantially horizontal layer of electromagnets arranged in a plane normal or substantially normal to the vertical axis of the container 220. As indicated by the number of magnetic structures, the exemplary magnetic assembly 205 can comprise a plurality of vertically-spaced layers of magnetic structures, including 2 magnetic structures, 3 magnetic structures, 4 magnetic structures, 5 magnetic structures, 10 magnetic structures, 20 magnetic structures, or more. Additionally, it will be appreciated that although four electromagnets 210*a-d* are depicted as being associated with each magnetic structure 210 in FIG. 5, the present teachings are not so limited as any number of electromagnets capable of operating according to various aspects of the applicant's teachings can be used as further described herein. Moreover, the magnetic structures of each layer need not be identical. For example, though electromagnets of a layer of magnetic structures can be disposed such that their centerline extends toward the container 220, in some aspects the electromagnets of another layer can have a different configuration. By way of example, the electromagnets of a layer of magnetic structures can be oriented substantially orthogonally (or another non-zero angle) relative to the plane containing the centerline of the electromagnets.

The magnetic structures can be formed from a plurality of electromagnets disposed around the container 220 at one or more different vertical heights, with each electromagnet being individually controlled to generate a desired changing magnetic field (e.g., oscillating magnetic field, rotating magnetic field) within the container 220 effective to influence the ferrimagnetic particles disposed therein. Based on the selective application of electrical signals to the plurality of electromagnets surrounding the container 220, the ferrimagnetic particles can be influenced to rotate, spin, move horizontally side-to-side, and/or vertically up-and-down within the fluid sample by the combined effect of the magnetic fields generated by the various electromagnets. By way of example, the signals applied to the electromagnets 210a-d of each magnetic structure 210 (e.g., in a single horizontal layer) can be configured to generate changing magnetic fields substantially in the x-y plane, while the signals applied to the electromagnets of the different magnetic structures, can result in changing magnetic fields exhibiting a z-direction or vertical component. In this manner, the combined effect of the plurality of electromagnets can produce a magnetic field within the container 220 with different characteristics, such as different strengths and/or directionality so as to rapidly and efficiently mix the sample and/or capture target analytes within the sample, by way of non-limiting example.

In some examples, the vertical position of one or more of the magnetic structures 210 can be adjustable, for instance, to process different sample volumes and/or to affect a characteristic of a magnetic field generated by the magnetic assembly 205. By way of example, in some aspects, the magnetic structure 210, can be vertically adjustable according to various aspects of the applicant's teachings depending, for example, on the volume of the sample in the container 220. It will be appreciated, for example, that the position of the magnetic structure 210 with respect to the ferrimagnetic particles and/or other magnetic structures can affect the location, strength, intensity, direction, or other characteristics of the magnetic field generated by the magnetic assembly 205 within the container 220. In this manner, the magnetic structure 210 can be moved to various heights in order to optimally process fluids of different volumes and/or to alter the characteristics of a magnetic field generated in the container 220. Though the above description provides for the movement of a single magnetic structure relative to another magnetic structure of the magnetic assembly 205, it will be appreciated that any number of layers of magnetic structures 210 can be moved by a positioning element (not shown) that is configured to adjust the position of one or more electromagnets 210a-d or one or more of magnetic structures 210 relative to one another, and/or to adjust the position of the entire magnetic assembly 205 relative to the container 220. Non-limiting examples of positioning elements can include rotary actuators, linear actuators, servomotors, electronic motors, or the like. In some examples, the volume of the sample in the container 220 can be measured by measuring a device (not shown) such that the positioning element can automatically adjust the position of one or more electromagnets 210a-d and or magnetic structures 210 based on the measured volume of the sample in the container 220 and/or the requirements of the sample processing protocol. In some examples, the positioning element can be configured to adjust the position of one or more electromagnets 210a-d and/or magnetic structures 210 based on user input, manual input, a sample processing protocol, and/or a pre-set volume.

Each electromagnet in the magnetic assembly can generate a changing magnetic field when the electrical current passing through the solenoid of each electromagnet is AC. As the current changes direction through the coil of the solenoid, the magnitude and/or direction of the resulting magnetic field can change. In some examples, each electromagnet 210a-d of the magnetic structure 210 can receive an alternating current that is phase shifted by a predetermined amount compared to the alternating current that the other electromagnets of the magnetic structure 210 receive. In this way, each electromagnet can generate a changing magnetic field. The interference of each of the generated changing magnetic fields in the container can be a rotating magnetic field.

C. Control Component

In accordance with various aspects of the applicant's present teachings, a control component can be coupled to the magnetic assembly for controlling the changing magnetic field. The control component can be configured to differentially actuate the electromagnets of the magnetic assembly via the application of one or more radio frequency (RF) signals, direct current (DC) signals, alternating current (AC) signals, or the like. By way of non-limiting example, in some aspects, the control component can be configured to control the magnetic field generated by each of the plurality of electromagnets via applying a square waveform (of the current) to each of the plurality of electromagnets. For example, the square waveform can exhibit a frequency in a range of about 0.5 Hz to about 300 Hz, or between about 200 Hz and about 300 Hz. Alternatively, in some aspects, the control component can be configured to control the magnetic field generated by each of the plurality of electromagnets, with the AC signals applied to the plurality of electromagnets exhibiting different phase delays relative to one another so as to effect the desired movement of the ferrimagnetic particles within the sample. Each electromagnet can generate a changing magnetic field. For example, an AC waveform applied to an electromagnet can cause the generation of an oscillating magnetic field or a rotating magnetic field. The control component can be configured to adjust the magnetic field intensity.

In some examples, the frequency can be tuned, by the control component, to the responsiveness of the ferrimagnetic particle. For example, slow moving ferrimagnetic particles can require a lower frequency so that they have more time to move toward the magnet, while fast-moving ferrimagnetic particles require a higher frequency so that they do not immediately move to the walls of the container. the rate of speed of the particles can involve multiple variables, for example, the magnetic responsiveness of the core material, the percentage of magnetic material in the core, the particle size, and the viscosity of the fluid (among other variables). As an example, ferrimagnetic particles of sizes of about 1 µm to about 2 µm, can be subjected to magnetic fields tuned to a frequency of about 200 Hz. In some examples, much higher frequencies can be used to cause the bead to vibrate rather than mix in a circle which could be used for DNA fragmentation.

In some examples, the control component can be configured to control the magnetic field generated by each of the plurality of electromagnets via applying a square waveform or a sine waveform to each of the plurality of electromagnets. Both the square waveform and the sine waveform can cause similar effects in the ferrimagnetic particles, however, the different waveforms have different power level usages in the device. This can be useful in minimizing the heat generation and electricity usage of the device.

The control component can be configured to cause the electromagnets to generate a certain magnetic field intensity. As described herein, the range of the field intensity could be the same range as any electromagnet as long as it is able to move the particles. In an example, the magnetic field has an intensity of between about 10 mT and about 100 mT, or between about 20 mT and about 80 mT, or between about 30 mT and about 50 mT. In some examples, more powerful electromagnets can be used to mix much less responsive microparticles. However, due to the power consumption and the need to fit close to small test tubes and microtiter plates, more powerful electromagnets are not practical under certain circumstances. The field can be focused into the sample as much as possible. Also, the electromagnets can be as close to the sample as possible since the strength of the magnetic field decreases as the square of the distance. In yet other examples, the control component can be configured to generate a magnetic field intensity of about 15 mT for highly responsive ferrimagnetic particles to about 90 mT for a short duration to jolt the ferrimagnetic particles. The magnetic field intensity can be in the range of 25 mT to 40 mT.

An example control component can be a class D amplifier that uses pulse-width modulation to control voltage at 22 KHz to create a 300 Hz sinusoidal current. In some examples, other suitable types of amplifiers capable of creating an appropriate current waveform can be used. The class D amplifier can work best and create the least amount of audible noise when using sinusoidal currents rather than square wave currents and triangle wave currents.

In some examples, the control component can generate currents in the electromagnets such that the electromagnet has a self-inductance of about 10 mH to about 50 mH. In other examples, the electromagnet can have a self-inductance of about 2 mH to about 15 mH.

In some aspects, the DC signals can be effective to isolate the electromagnets (e.g., draw the ferrimagnetic particles to one side and/or vertical level of the container) such that the sample, or a portion of the sample, can be withdrawn from the container without aspiration of the ferrimagnetic particles, by way of non-limiting example.

In some aspects, the at least one AC waveform applied to each of the plurality of electromagnets can exhibit a phase delay relative to the signals of the other plurality of electromagnets. For example, the phase delay can be a 30° phase delay, a 60° phase delay, a 90° phase delay, a 12° phase delay, a 15° phase delay, a 180° phase delay, a 210° phase delay, a 240° phase delay, a 270° phase delay, a 300° phase delay, a 330° phase delay, a 360° phase delay, and any value or range between any two of these values (including endpoints). In one aspect, for example, the control signal applied to the four electromagnets in each magnetic structure (e.g., in each horizontal layer) can comprise an AC waveform exhibiting a 90° shift relative to the adjacent electromagnets in that layer and/or the control signal applied to the four electromagnets in a magnetic structure can comprise an AC waveform exhibiting a 90° shift relative to its vertically-adjacent electromagnet in another magnetic structure (e.g., of a different horizontal layer). In some examples, the changing magnetic field generated by the magnetic assembly can be a rotating magnetic field. The AC waveform, applied to each of the plurality of electromagnets, exhibiting a phase delay, can cause the generation of a rotating magnetic field. In some examples, the rotating magnetic field can be a magnetic field that has moving polarities in which its opposite poles rotate about a central point or axis. It will be appreciated by those skilled in the art that the AC waveforms need not be necessarily be centered about 0 A.

Figure 6:
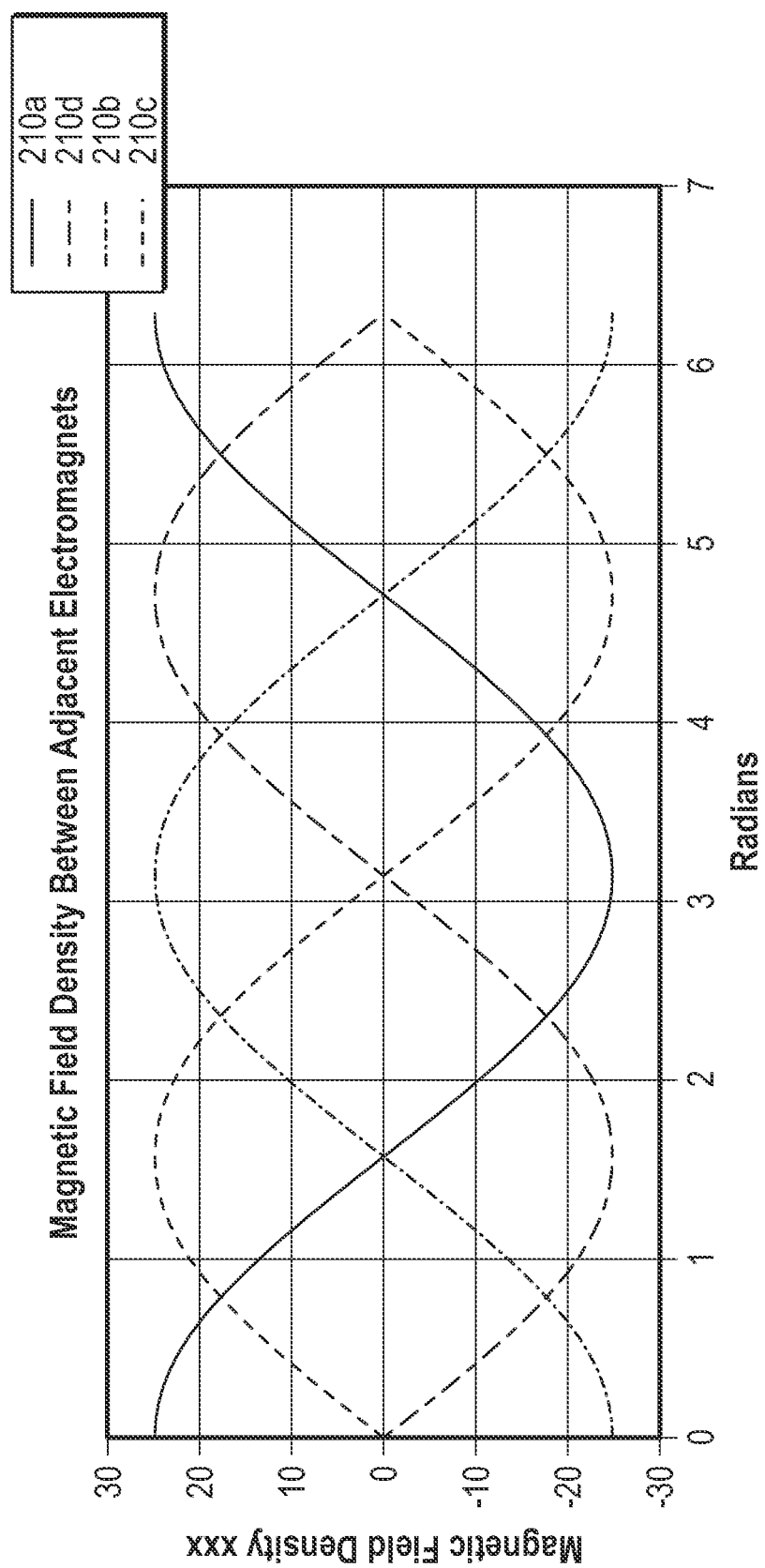
FIG. 6 is a plot of radians vs. magnetic field density and shows how a magnetic field density changes between adjacent electromagnets according to the instant disclosure.

FIG. 6 shows an example magnetic field density between adjacent electromagnets. The graph includes the magnetic field density between 210a and 210c, 210c and 210d, 210d and 210b, as well as 210b and 210a. The x-axis of the plot shows radians, whereas the y-axis shows magnetic field density in mT. The AC waveform applied to each of the plurality of electromagnets by the control component, as described herein, can generate changing magnetic fields. In this example, the magnetic field density between 210a and 210c can be 25 mT at 0 radians. The magnetic field density between these two electromagnets oscillates as a sine wave, as shown in FIG. 6. The magnetic field density can oscillate between each of the adjacent electromagnets.

With reference again to FIG. 5, the exemplary sample processing system 200 additionally includes a control component 230 operatively coupled to the magnetic assembly 205 and configured to control the changing magnetic fields (e.g., oscillating magnetic fields, rotating magnetic fields) produced by the plurality of electromagnets 210a-d. In various aspects, the control component 230 can be configured to control one or more power sources (not shown) configured to supply an electrical signal to the plurality of electromagnets 210a-d.

In some examples, the control component 230 can operate to regulate the magnetic field produced by each of the electromagnets 210a-d by controlling the amplitude, frequency, and direction of the electrical current passing through a solenoid of each of the electromagnets 210a-d. In some examples, the electrical signal can be in the form of radio frequency (RF) waveforms, DC current, AC current (e.g., a square waveform), or the like. Indeed, it will be appreciated that any type of electrical current capable of operating according to various aspects of applicant's teachings to promote mixing of the fluid sample are contemplated herein. By way of example, a DC signal can additionally or alternatively be applied to one or more the electromagnets so as to draw magnetic particles to one or more sides of the container (and out of the bulk fluid) so as to aid in fluid transfer from the container after the mixing step and/or prevent the aspiration of the magnetic particles, by way of non-limiting example.

In various aspects, each electromagnet 210a-d in the magnetic structure 210 can be individually addressed and actuated by the control component 230. For example, the control component 230 can supply RF or AC electrical signals of different phases to each of the one or more of the electromagnets such that one or more of the electromagnets generate a different magnetic field relative to the other of the electromagnets. The plurality of electromagnets 210a-d can be disposed at different locations relative to the container 220, thus the orientation of the magnetic field generated by each electromagnet can differ even when the same electrical signal is applied thereto. For example, because electromagnetic pairs can be arranged on opposed sides of the container, the magnetic field generated by the electrode in each pair can be in the same direction.

In this manner, the magnetic field generated by the magnetic assembly 205 within the container 220 can be rapidly and effectively controlled to manipulate the movement of ferrimagnetic particles within the sample. In some examples, the electrical signals and the characteristics thereof (e.g., phase shifts, frequency, amplitude) can be applied to the various electromagnets according to the sample processing protocol. It will be appreciated in light of the present teachings that the magnetic assembly 205 can be utilized to manipulate the ferrimagnetic particles within the sample in various processes including, without limitation, protein assays, sample derivatization (e.g., steroid derivatization, sample derivatization for gas chromatography, etc.), and/or sample purification and desalting. Following this processing, processed samples (e.g., fluids) can be delivered to various analytical equipment (not shown), such as a mass spectrometer (MS), or any other suitable analyzer described herein, for analysis.

In various aspects, the control component can be any type of device and/or electrical component capable of actuating an electromagnet. For example, in some aspects, the control component can include or be coupled to a logic device (not shown) and/or a memory, such as a computing device configured to execute an application configured to provide instructions for controlling the electromagnets of the magnetic structure(s) 145. In some examples, the application can provide instructions based on operator input and/or feedback from the sample processing system 200. In some examples, the application can include and/or the memory can be configured to store one or more sample processing protocols for execution by the control component.

In various related aspects, the sample processing system can include at least one memory operatively coupled to the controller configured, for example, to store at least one sample processing protocol for execution by the controller. In some aspects, the system can be configured to process the at least one fluid by mixing it. In some aspects, the system can be configured to process the at least one fluid by performing fluid separation to capture at least one target analyte within the at least one fluid.

In some examples, the control component can be configured to perform degaussing. Degaussing is the process of decreasing and/or eliminating a remnant magnetic field. The control component can be configured to perform moderate degaussing to further reduce the amount of residual magnetism in the ferrimagnetic particles.

D. Collection Component

In some examples, a collection component can be disposed at the periphery of the container. The collection component can be capable of collecting the ferrimagnetic particles in the container, thereby allowing the ferrimagnetic particles to be separated from the sample.

The collection component can comprise a magnet. For example, the collection component can comprise a magnet comprising a ferromagnetic material. In some examples, the collection component can be brought to the periphery of the container after the ferrimagnetic particles have been mixed throughout the sample.

In some examples, the collection component can be an electromagnet. The electromagnet can be operatively coupled to the control component, the control component capable of controlling the electromagnet. The electromagnet can receive a DC electrical signal from the control component, thereby generating a static magnetic field. The ferrimagnetic particles can be manipulated to move a particular area in the container through the influence of the applied static magnetic field.

In other examples, the collection component can be the magnetic assembly. For example, one or more of the electromagnets of a magnetic structure can receive a DC electrical signal from the control component, thereby generating a static magnetic field. The ferrimagnetic particles can be manipulated to move a particular area in the container through the influence of the applied static magnetic field.

E. Analyzer

The sample processing system can also include an analyzer. In some examples, the analyzer can be disposed adjacent to the magnetic assembly. In other examples, the analyzer can be operatively coupled to the container. It will be appreciated by those skilled in the art that any suitable analyzer can be used to analyze the analyte or the sample. The analyzer can include any suitable instrument that is capable of analyzing a sample such as a biological sample. Examples of analyzers include mass spectrometers, immunoanalyzers, hematology analyzers, microbiology analyzers, and/or molecular biology analyzers. PCT Application No. PCT/US2018/033927 discloses an integrated sample processing system with multiple detection capability, and is hereby incorporated by reference herein in its entirety.

In some examples, the analyzer can be an immunoanalyzer used for detecting a label (chemoluminescent, electrochemiluminescent, fluorescent, radioactive isotope, DNA, etc.) or using a label free system. Other types of analyzers can include hematology analyzers, microbiology analyzers, chemistry analyzers, urine analyzers, biochemical analyzers, and/or a molecular biology analyzers. When analyzing a biological sample, one or more of these types of analyzers, in any suitable combination, can be used to analyze the biological sample.

A hematology analyzer can be used to perform complete blood counts, erythrocyte sedimentation rates (ESRs), and/or coagulation tests. Automated cell counters sample the blood, and quantify, classify, and describe cell populations using both electrical and optical techniques.

A microbiology analyzer can function as a diagnostic tool for determining the identity of a biological organism. In some examples, a microbiology analyzer can identify an infecting microorganism. Such analyzers can use biochemicals in a plurality of small sample test microwells in centrifugal rotors that contain different substrates, or in multi-well panels, depending on the type of test being performed.

A molecular biology analyzer can be a device which can analyze a biological sample at its molecular level. An example of a molecular biology analyzer can include a nucleic acid analyzer such as a DNA analyzer.

A chemistry analyzer can run assays on clinical samples such as blood serum, plasma, urine, and cerebrospinal fluid to detect the presence of analytes relating to disease or drugs. A chemistry analyzer can use photometry. In photometry, a sample is mixed with the appropriate reagent to produce a reaction that results in a color. The concentration of the analyte determines the strength of color produced. The photometer shines light of the appropriate wavelength at the sample and measures the amount of light absorbed, which is directly correlated to the concentration of the analyte in the sample. Another analytical method used in a chemistry analyzer is the use of ion selective electrodes (ISE) to measure ions such as $Na^+$, $K^+$, $Cl^-$, and $Li^+$. An ISE is a sensor that determines the concentration of ions in a solution by measuring the current flow through an ion selective membrane.

A "mass spectrometer" is an instrument which can measure the masses and relative concentrations of atoms and molecules. One example of a mass spectrometer makes use of the basic magnetic force on a moving charged particle. Basically, the instrument ionizes a sample and then deflects the ions through a magnetic field based on the mass-to-charge ratio of the ion. The mass spectrum can then be used to determine the elemental or isotopic signature of a sample, the masses of particles and of molecules, and to elucidate the chemical structures of molecules, such as peptides and other chemical compounds. Commercially available mass spectrometers can be categorized based on how they sector mass selection, including time-of-flight, quadrupole MS, ion traps (including 3D quadrupole, cylindrical ion traps, linear quadrapole ion traps, orbitraps), Fourier transform ion cyclotron resonance (FTMS), etc. Alternatively, they can be sectored based on ion source (laser desorption, matrix assisted laser desorption, thermal ionization, plasma, spark source, etc.) or detectors (electron multipliers (such as Faraday cups and ion-to-photon detectors), inductive detectors, etc.). In an example, the mass spectrometer can be a triple quadrupole mass spectrometer.

III. METHOD

A method for processing a sample can be performed using the ferrimagnetic particles of the disclosure. The methods of the disclosure comprise providing a container comprising ferrimagnetic particles and a sample. The container is then subjected to a changing magnetic field generated by a magnetic assembly. The sample is then processed by the movement of the ferrimagnetic particles in the container. In some examples, the changing magnetic field can be a rotating magnetic field. In other examples, the changing magnetic field can be an oscillating magnetic field.

In some examples, as the ferrimagnetic particles move through the container, the ferrimagnetic particles can bind to cells located in the sample. Once the ferrimagnetic particles are bound to the cells, the ferrimagnetic particles can continue to move due to the influence of the changing magnetic field generated by the magnetic assembly. Thus, the cell can be moved throughout the sample. In other examples, the ferrimagnetic particles can bind to cells for collection collection/concentration of the cells, as described herein. In yet other examples, the ferrimagnetic particles can bind to cell surface molecules for identification of the cells. The ferrimagnetic particles can also be used to pull bound surface molecules out of a cellular membrane. A similar process can be used for cell modification.

In other examples, the ferrimagnetic particles can be used to puncture the cellular membrane or cell wall to get the particles or reagents inside the cell or nucleus (physical cell permeabilization rather than reagent-based). Additionally, the ferrimagnetic particles can be used to physically break apart living or dead cells or cellular components. Further, the ferrimagnetic particles can be used to selectively destroy one type of cell over another. In some examples, the ferrimagnetic particles can be used to break apart large molecules like DNA/RNA through collisions between the ferrimagnetic particles and the large molecules. In other examples, the ferrimagnetic particles can be used to accelerate the resuspension of lyophilized reagents or particles.

After subjecting the container to a changing magnetic field, the ferrimagnetic particles can be collected, with a collection component, as described herein. After the ferrimagnetic particles have been collected with the collection component, the sample processing protocol can further comprise eluting at least a portion of the sample from the container. The portion of the sample can be eluted using any suitable method.

After the portion of the sample is eluted, an analysis can be performed. The analysis can be performed by an analyzer, as described above. In other examples, the ferrimagnetic particles can be used to accelerate chemical reactions like enzymatic digestions or protein binding. As the ferrimagnetic particles move, due to the influence of the changing magnetic field, the ferrimagnetic particles can cause further movement in the container (e.g., via collisions with other particles in the container), thus mixing the sample and causing the acceleration of a chemical reaction.

Furthermore, in some examples, the sample can comprise inorganic compounds or tiny objects. The ferrimagnetic particles can be moved through the container by the changing magnetic field generated by the magnetic assembly. The ferrimagnetic particles can bind to the inorganic compounds or the tiny objects in the sample. Further analysis can then be performed as described herein. In other examples, the sample processing system can be used with the ferrimagnetic particles, which can be highly magnetically responsive, which can be used to mix less responsive or nonmagnetic particles or reagents disposed in the sample.

In some examples, the ferrimagnetic particles can be a ferrofluid with magnetic properties as described herein. The sample processing system can mix the ferrofluid throughout the sample using a changing magnetic field.

Multiple particle types can be disposed in the container with different magnetic responsiveness. For example, two populations of ferrimagnetic particles, such as a first population of ferrimagnetic particles comprising a ferrite core comprising MnZn ferrite as well as a second population of ferrimagnetic particles comprising a ferrite core comprising NiZn ferrite, can be disposed in the container. Each population of ferrimagnetic particles can be used to selectively separate multiple analytes from the same sample (e.g., separate a highly responsive DNA-binding particle first followed by a slowly responsive protein-binding particle). Furthermore, each population of ferrimagnetic particles disposed in the container can be used for any purpose as described herein.

In yet other examples, the ferrimagnetic particles can be placed in a continuous flow system, as described herein, allowing for the continuous mixing of reagents flowing through the mix chamber.

IV. KIT

In accordance with various aspects of the present teachings, a kit can comprise ferrimagnetic particles and a container. The ferrimagnetic particles can be disposed in the container. The kit can further comprise reagents for desired analytic methods. The reagent can be any suitable reagent (e.g., precipitating reagents, wash buffers, elution buffers, and the like) that can be used while processing or analyzing a sample, for example, analyzing the sample for the presence of a particular analyte, such a biological molecule. In other examples, the kit can further comprise any portion of the sample processing system, as described herein.

V. EXAMPLES

Example 1. Preparation of Solid Phase Reversible Immobilization (SPRI) Beads for DNA Isolation The sample processing system according to examples of the disclosure can be used to isolate a nucleic acid, such as DNA, from a sample. This process can comprise two main parts, a preparation phase and a procedure phase.

The preparation phase began with a SPRI bind buffer solution. The SPRI bind buffer solution included, for example, PEG (polyethylene glycol) and salt (NaCl). Carboxyl-coated ferrimagnetic particles, prepared as described in Example 6, were resuspended in the SPRI bind buffer solution. The concentration of the ferrimagnetic particles was normalized to that of a standard AMPure XP™ bind buffer, supplied as part of the product available under the trade designation AMPure XP™, available from Beckman Coulter, Brea, Calif.

After preparing the SPRI bind buffer solution, a fresh 80% ethanol solution was prepared. A DNA sample was prepared by combining a 20 µL aliquot of 100 bp DNA ladder, available under catalogue number N3231S from New England BioLabs, INC., Ipswich, Mass., with 580 µL DI water to create a 30:1 dilution. Next, the power level of the control component is set to 75% and the frequency to a 200 Hz sine wave. The plates and tubes were kept lidded as much as possible to reduce variation due to evaporation.

After the preparation phase was completed, the procedure phase began. In some examples, in parallel to the procedure below, the same procedure was be performed manually with standard AMPure XP™ bind buffer as a control. Some of the diluted DNA was reserved as another control.

50 μL of the diluted DNA and 90 μL of the ferrimagnetic particle mixture (e.g., SPRI bind buffer solution) was added to a 0.5 mL Eppendorf tube (e.g., the container) to selectively precipitate the DNA in the sample. The sample processing system, described herein was used to fully mix the contents of the Eppendorf tube to allow binding of the precipitated DNA to the ferrimagnetic particles.

After mixing the sample and the ferrimagnetic particles, the sample was incubated for 5 minutes while keeping the ferrimagnetic particles suspended. Next, a magnet (e.g., the electromagnets as described herein) was used to separate the ferrimagnetic particles from the solution until clear, to allow removal of the supernatant.

Next, 200 μL ethanol was added to the container. Then, the sample processing system was used to fully mix the contents of the container, separate the ferrimagnetic particles, and remove any supernatant.

50 μL deionized (DI) water was added to the container to elute the DNA off the ferrimagnetic particles. The sample processing system was used to fully mix the sample. The sample was then incubated for 2 minutes while keeping the ferrimagnetic particles suspended. Then, the magnet was used to separate until clear and transfer the eluent to a new plate. After transferring the eluent to the new plate, the eluent DNA concentration was measured using, for example, Nanodrop or PicoGreen assay. The concentration to the initial diluted DNA concentration and the manually executed AMPure XP™ elution concentration was then compared.

Various examples describing methods for making and coating further SPRI beads are provided below.

Example 2. Magnetic Core Synthesis: Synthesis of Magnetite ($Fe_3O_4$) Core

A magnetic core of a magnetic particle was prepared by mixing 2.16 g $FeCl_3.6H2O$ and 64 ml ethylene glycol in a 200 mL beaker to produce a light brown solution with no solids. 5.76 g of sodium acetate and 1.6 g of polyethylene glycol (PEG 400) were added to the solution, which is subsequently stirred for 30 minutes. The stirred solution was transferred to a 100 mL autoclave reactor and heated therein to 180° C. for 36 hours. After 36 hours, heating was stopped and the autoclave was cooled to room temperature. The resulting magnetite core particles with average size around 100 nm were collected using a permanent magnet and were subsequently washed with water for 5 times.

Example 3. Bead Encapsulation: Silica Coating on Magnetic Core

An encapsulated magnetite core was prepared by dispersing 20 g of 100 nm magnetite core prepared according to Example 2 in 800 ml methanol in a 1 L beaker. The mixture was sonicated for 30 minutes to achieve a uniform suspension. 370 ml of 28% ammonia hydroxide was added into the suspension, which was then stirred for 30 minutes. Following sonication, a liquid mixture including 0.5 mL of tetraethyl orthosilicate and 4.5 mL of methanol was added into the suspension dropwise under further sonication over a time span of 0.5 hrs. following sonication the beaker was covered and the suspension was continuously stirred for 15 hrs. Following stirring the encapsulated beads were captured with a permanent magnet. The encapsulated beads were then washed 5 times with water. The beads were then dried in an oven at 80° C. for 24 hrs.

Example 4. Surface Functionalization: Carboxylation of Silica Coated Magnetic Core A carboxylated silica coated magnetic core was prepared by dispersing 4 g of silica coated magnetite core particles prepared according to Example 3 dispersed with 150 mL toluene in a 500 mL flask under stirring. 20 g of (3-triethoxysilyl)propylsuccinic anhydride was added under stirring to the flask. 0.2 g imidazole was then added under stirring to produce a uniform suspension. The suspension was refluxed at around 114° C. under stirring for 15 hrs. Following refluxing, the suspension was cooled to room temperature and a permanent magnet was used to collect solids from the suspension. The solids were washed first with methanol once and then with water 5 times and transferred to a 500 ml flask. 150 ml of 0.1 M acetic acid in water was added to the flask under stirring to get a uniform suspension. The suspension was heated to 90° C. for 15 hrs. The suspension was cooled to room temperature. A permanent magnet was used to collect solids from the suspension. The solids were washed with water 5 times and dried in oven at 60° C. for 15 hrs.

Example 5. Bead Encapsulation: Polymer Coating on Magnetic Core

An encapsulated polymer coated magnetic core was prepared by dispersing 4 g of 100 nm magnetite core prepared according to Example 2 in 100 ml water in a 500 ml flask under stirring. 10 mL of acrylic acid was added to the flask under stirring along with 1 g $K_2S_2O_8$ to get a uniform suspension. The suspension was heated to 80° C. for 15 hrs under stirring. The suspension was then cooled to room temperature. A permanent magnet was used to collect the solids from the suspension. The collected solids were washed 5 times with water and the dried at 60° C. for 15 hrs.

Example 6. Bead Encapsulation: Polymer Coating on Magnetic Core 0.5 g of PMA (poly-methyl vinyl ether alt-meleic anhydride, MW 260,000), 30 g of acetone and 2.0 grams of 100 nm magnetite core were prepared according to Example 2 and were added to a 250 mL flask and stirred overnight. 30 g of dioxane was added to the flask. The suspension in the flask was heated up to 80° C. for 10 hours. The product was collected using a permanent magnet and washed with dioxane once and methanol for 3 times. The washed solid product was transferred to a 250 mL flask and 85 g of water and 15 g of 1 M acetic acid (in water) were added. The suspension in the flask was heated to 80° C. for 3 hours. The solid product was collected and washed with water for 5 times. The final solid product was dried in oven at 60° C. overnight.

Example 7. Surface Functionalization: Carboxylation of Magnetic Core 2 g 100 nm magnetite core, prepared according to Example 2 were mixed with 5 g (3-triethoxysilyl)propylsuccinic anhydride and 100 mL toluene in a flask. The mixture was stirred to prepare a uniform suspension. The suspension was then heated to reflux for 24 hrs under stirring. After 24 hrs, heating was stopped and the suspension was cooled down to room temperature. The product was then collected using a permanent magnet. The product was washed with methanol once followed by washing with water for 3 times. The product was transferred to a flask with 100 mL 0.1 M acetic acid in water and stirred to produce a uniform suspension. The suspension was then heated to 90° C. for 15 hrs under stirring. After 15 hrs, Heating was stopped and the suspension was allowed to cool to room temperature. The product was collected using a permanent magnet. The product was then washed with water for 3 times. The product was then dried in an oven at 60° C. overnight.

Example 8. Preparation of Trypsin Immobilized Magnetic Beads 0.5 g poly(acrylic acid) coated magnetic beads, prepared according to Example 5 were mixed with 20 mL 0.1 M sodium phosphate buffer (pH 7.5), and 50 mg TPCK-treated trypsin in a flask. The mixture was stirred to prepare a uniform suspension. 200 mg of 1-cyclohexyl-3-(2-morpholinoethyl)carbodiimide metho-p-toluenesulfonate was added to the suspension. The suspension was kept at 4° C. for 24 hrs under stirring. The product was collected using a permanent magnet and washed with water for 5 times. The product was then re-dispersed in 50 mM acetic acid in water and stored at 4° C.

Example 9: Isolation of Nucleic Acids

The sample processing system according to examples of the disclosure can be used to measure an eluent DNA concentration. This process included two main parts, a preparation phase and a procedure phase.

The preparation phase began with a SPRI bind buffer solution. The SPRI bind buffer solution included, for example, PEG (polyethylene glycol) and salt (NaCl). Carboxyl-coated magnetic particles prepared according to Example 6 were then resuspended in the SPRI bind buffer solution. The concentration of the ferromagnetic particles was normalized to that of a standard AMPure XP™ bind buffer, supplied as part of the product available under the trade designation AMPure XP™, available from Beckman Coulter, Brea, Calif.

After preparing the SPRI bind buffer solution, a fresh 80% ethanol solution was prepared. Next, a DNA sample was prepared by combining a 20 µL aliquot of 100 bp DNA ladder, available under catalogue number N3231S from New England BioLabs, INC., Ipswich, Mass., with 580 µL DI water to create a 30:1 dilution. Next, the power level of the control component was set to 100% and the frequency to a 50 Hz sine wave. The plates and tubes were kept lidded as much as possible to reduce variation due to evaporation.

After the preparation phase was completed, the procedure phase began. In some examples, in parallel to the procedure below, the same procedure were performed manually with standard AMPure XP™ bind buffer as a control. Some of the diluted DNA was reserved. as another control.

50 µL of the diluted DNA and 90 µL of the ferrimagnetic particle mixture (e.g., SPRI bind buffer solution) was added to a 0.5 mL polymerase chain reaction (PCR) vessel (e.g., the container) to selectively precipitate the DNA in the sample. The sample processing system, described herein was used to fully mix the contents of the container to allow binding of the precipitated DNA to the magnetic particles.

After mixing the sample and the ferrimagnetic particles, the sample was incubated for 5 minutes while keeping the ferrimagnetic particles suspended. Next, a magnet (e.g., the electromagnets as described herein) was used to separate the ferrimagnetic particles from the solution until clear, to allow removal of supernatant.

200 µL 80% ethanol was added to the container. Then, the sample processing system was used to separate the ferrimagnetic particles, and removal of the supernatant.

50 µL deionized (DI) water was added to the container to elute the DNA off the magnetic particles. The sample processing system was used to fully mix the sample. The sample was then incubated for 2 minutes while keeping the ferrimagnetic particles suspended. Then, the magnet was used to separate until clear and transfer the eluent to a new plate. After transferring the eluent to the new plate, the eluent DNA concentration was measured using, for example, NanoDrop or PicoGreen assay. The concentration to the initial diluted. DNA concentration and the manually executed AMPure XP™ elution concentration was then compared.

Figure 7:
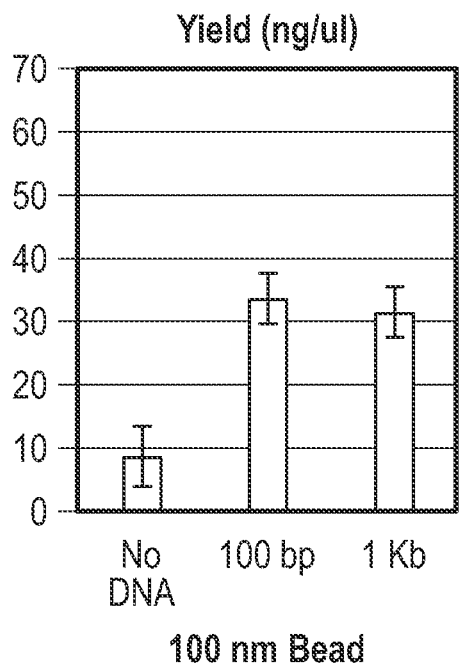
FIGS. 7-10 are plots showing DNA concentration according to various aspects of Example 8 according to the instant disclosure
Figure 8:
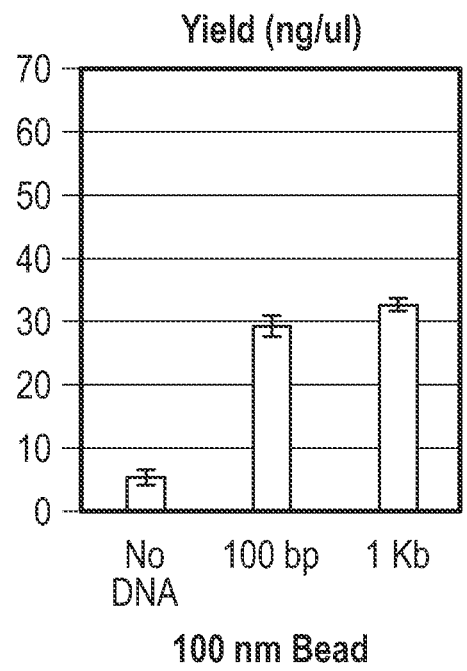
Figure 9:
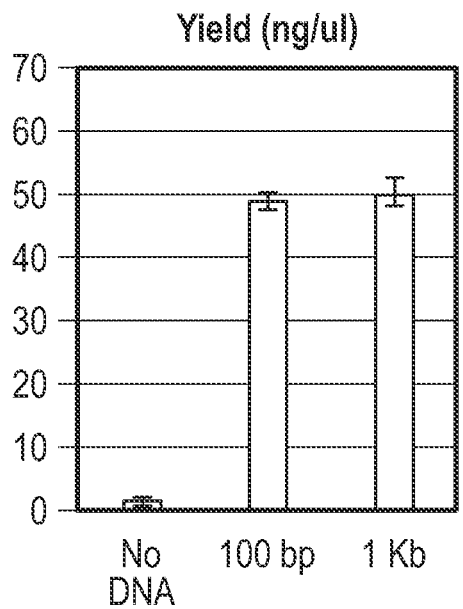
Figure 10:
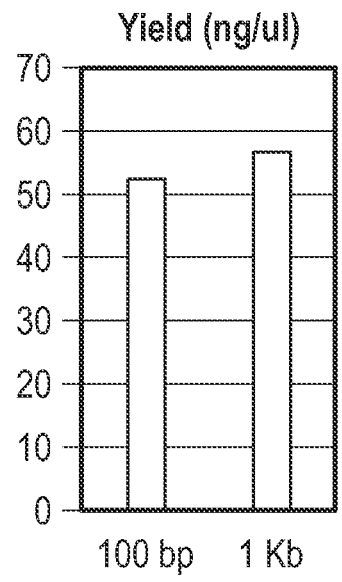

The amount of DNA isolated is shown in FIG. 7 for the magnetic bead in the mixer. For comparison, FIG. 8 shows the amount of DNA isolated with the magnetic bead using a corresponding procedure, but with no mixing. As a further Example FIG. 9 shows the amount of DNA that was isolated using a manual mixing procedure with a control bead. The control bead was a paramagnetic bead designated as comparative bead 1, below. FIG. 10 shows the input levels of DNA in each Example.

Example 10. Trypsin Digestion

Figure 11:
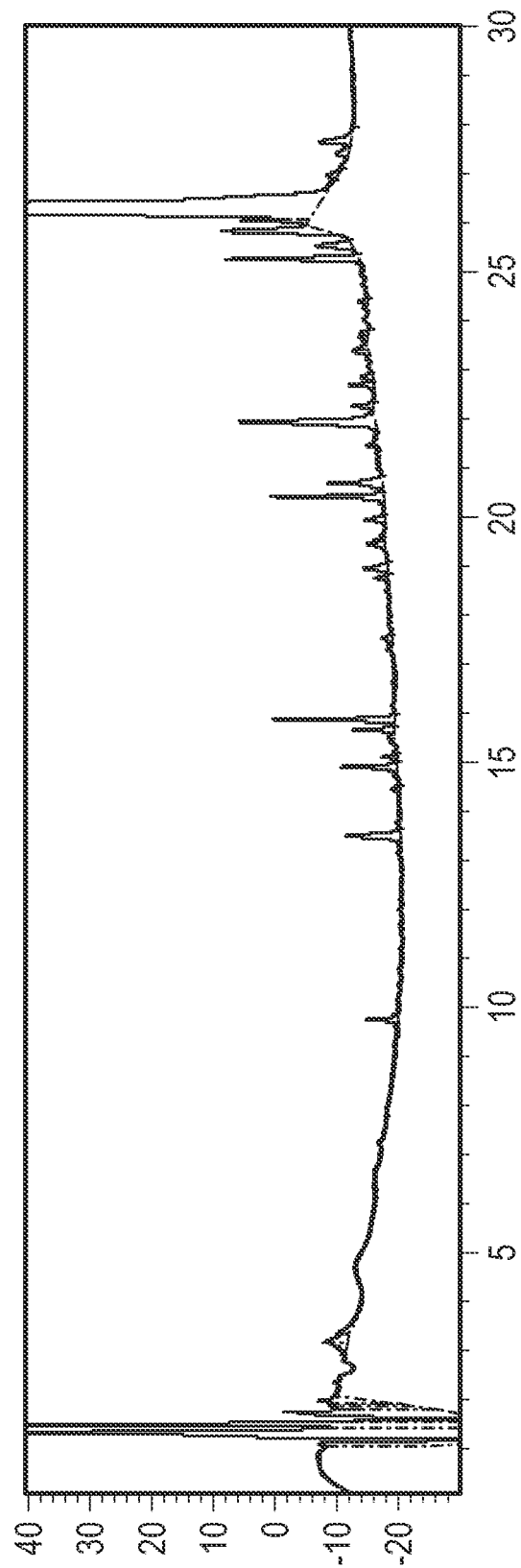
FIG. 11 shows a high performance liquid chromatography (HPLC) output of a trypsin digestion according to Example 9 according to the instant disclosure.

Magnetic beads were used to digest trypsin according to the following procedure. Phosphate-buffered saline (PBS) stock, available under the trade designation 10×PBS™ available from Invitrogen, Carlsbad, Calif. was diluted 10 times. 5 mg/mL of cytochrome C protein solution in PBS was prepared. 0.122 mL PBS, 0.125 mL 5 mg/mL cytochrome C protein solution were placed in a 1.5 mL vial. Trypsin immobilized magnetic beads, prepared according to Example 7 were washed with water 3 times. The water was removed to get a bead pellet. 0.01 mL (pellet volume) trypsin immobilized beads were added to the 1.5 mL vial. The vial was mounted on the magnetic mixer and mixed for 20 min at 150 Hz and 80 mT to conduct trypsin digestion. Digestion was stopped after mixing by adding 0.0278 mL 1% formic acid. A 0.1 mL solution was taken for HPLC analysis. The results of the HPLC analysis are shown in FIG. 11, which shows the digested products. The HPLC conditions were as follows:

Mobile phase: A-0.1% TFA/FA in Water; B-0.1% TFA/FA in ACN.
Gradient: 0-0.5 min 1% B, 1-50% B in 30.5 min, 50% B in 5 min, 3 min clean up at 95% B, 5 min re-EQ at 1% B.
Flow rate: 0.3 mL/min.
Temperature: 40° C.
UV detector: 214 nm.
Injection: 2 µl.

Example 11. Characterization of Suitability of Magnetic Beads

Various magnetic beads were studied for their ability to be 1) magnetically responsive enough to mix in water, 2) be magnetically responsive enough to be able to mix in a solution of a polyethylene glycol, sodium chloride, water, 3) for their ability to not clump magnetically, 4) for their ability to be coated with a carboxyl, 5) for their ability to isolate nucleic acid, and 6) for their ability to isolate nucleic acid in a sufficient yield.

To assess properties 1-3, 5 μL of a solution of the various beads was added to 140 μL of water or the solution of a polyethylene glycol, sodium chloride, water, and in a well. To determine if they were magnetically responsive enough to mix, the beads were pulled magnetically down to the bottom of the well and then mixed with the electromagnetic mixer. If the particles appeared to disperse fully up to the surface of the liquid, it was determined that the particles were responsive enough to mix as indicted in Table 2 with a "y", if they did not mix into solution, the particles were determined to not be magnetically responsive enough to mix as indicated in Table 2 with an "n". If, during electromagnetic mixing, the magnetic particles did not aggregate into a clump of particles, the particles were deemed not to clump, as indicted in Table 2 with a "y", if there were clumps present during mixing, the particles were deemed to clump as indicated in Table 2 with an "n". To determine if the beads could be carboxyl coated as in 4), the beads were subjected to a procedure substantially in line with Example 4, beads that could be carboxyl coated are so identified in Table 2 with a "y", beads that could not be carboxyl coated are so indicated in Table 2 with an "n".

To determine if the beads could be used to isolate DNA as in 5) a 50 μL sample of DNA was added to the well and mixed with the beads. Beads that did isolate DNA are so indicted in Table 2 with a "y", beads that did not isolate DNA are so indicated in Table 2 with an "n". To determine if the beads could be used to isolate DNA to achieve a sufficient yield of between 60% to 90% of the input DNA as in 6) the yield was calculated and if sufficient, indicted in Table 2 with a "y", beads that did not isolate DNA to achieve a sufficient yield are so indicated in Table 2 with an "n".

Table 1 provides a list of various beads that were studied for the properties indicated above. The data shows that only the beads produced according to the instant disclosure provided each desirable aspect of the instant disclosure. Beads that differed in construction or magnetic properties proved unsuitable for use in a mixer as the beads failed any one of properties 1-6 or a combination thereof. Beads tested as comparative examples include beads produced by General Electric, Chemicell, Bangs Laboratories, Pelitex, Spherotech, Creative Diagnostics, Lumigen, Perfinity, Ocean NanoTech, Cospheric, and BioChain. Of the large amount tested none provided the desirable aspects 1-6. To illustrate this point, a sample of those beads, designed in Table 1 and Table 2 as comparative beads are compared to a magnetic bead of the instant disclosure.

TABLE 1

| Magnetic Beads | |
| --- | --- |
| Bead Label in Table 2 | Bead Description |
| Comparative Bead 1 | SpeedBead ™, available from General Electric, Boston, MA |
| Comparative Bead 2 | BioMagPlus COOH ™, available from Bangs Laboratories, INC, Fishers, IN |
| Comparative Bead 3 | ProMag 1 COOH ™, available from Bangs Laboratories, INC, Fishers, IN |
| Comparative Bead 4 | A 4.4 μm fluorescent ferromagnetic bead, available from Spherotech INC, Lake Forest, IL |
| Comparative Bead 5 | A 2.0 μm ferromagnetic bead, available from Spherotech INC, Lake Forest, IL |
| Comparative Bead 6 | A 2 μm bead designated WHM-S001 ™ available from Creative Diagnostics, New York, NY |
| Comparative Bead 7 | A 4 μm bead designated WHM-S002 ™ available from Creative Diagnostics, New York, NY |
| Bead 1 | A bead prepared according to Example 7 |

TABLE 2

Properties of Magnetic Beads

| | Comparative Bead 1 | Comparative Bead 2 | Comparative Bead 3 | Comparative Bead 4 | Comparative Bead 5 | Comparative Bead 6 | Comparative Bead 7 | Bead 1 |
| --- | --- | --- | --- | --- | --- | --- | --- | --- |
| Magnetically responsive enough to mix (1) | n | N | n | n | n | y | y | y |
| Magnetically responsive enough to mix well in buffers of PEG + NaCl, water, 80% ethanol (2) | n | n/a | n/a | n/a | n | n | n | y |
| Free of clumping magnetically (3) | y | n/a | n/a | n/a | y | y | y | y |
| Capable of carboxyl coating (4) | y | Y | y | n | y | y | y | y |
| Capable of isolating nucleic acid (5) | y | Y | y | y | y | n/a | n/a | y |
| Capable of isolating sufficient yield of nucleic acid (6) | y | n/a | n | n | n | n/a | n/a | y |

The above descriptions are illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any example can be combined with one or more features of any other example without departing from the scope of the disclosure.

A recitation of "a", "an" or "the" is intended to mean "one or more" unless specifically indicated to the contrary.

All patents, patent applications, publications, and descriptions mentioned above are herein incorporated by reference in their entirety.

Additional Aspects

The following exemplary aspects are provided, the numbering of which is not to be construed as designating levels of importance:

Aspect 1 provides a sample processing system comprising:
 a container configured to receive a sample for processing;
 ferrimagnetic particles disposed in the container;
 a magnetic assembly disposed about the periphery of the container for creating a changing magnetic field in the container, thereby moving the ferrimagnetic particles throughout the container; and
 a control component coupled to the magnetic assembly for controlling the changing magnetic field.

Aspect 2 provides the sample processing system of aspect 1, wherein the ferrimagnetic particles comprise a ferrite core.

Aspect 3 provides the sample processing system of aspect 2, wherein the ferrite core comprises a soft ferrite.

Aspect 4 provides the sample processing system of any one of aspects 2 or 3, wherein the ferrite core is selected from a group consisting of:
 cobalt ferrite;
 MnZn ferrite; and
 NiZn ferrite.

Aspect 5 provides the sample processing system of any one of aspects 1-4 further comprising:
 the sample disposed in the container.

Aspect 6 provides the sample processing system of aspect 5, wherein the ferrimagnetic particles further comprise a coating.

Aspect 7 provides the sample processing system of aspect 6, wherein the coating is a polymer layer or a silica layer for adjusting the density of the ferrimagnetic particles to be close to the density of a fluid.

Aspect 8 provides the sample processing system of any one of aspects 6 or 7, wherein the coating comprises a capture reagent for capturing an analyte in the sample.

Aspect 9 provides the sample processing system of aspect 8, wherein the capture reagent is an antibody.

Aspect 10 provides the sample processing system of any one of aspects 6-9, wherein the coating comprises a functional group for adsorbing nucleic acids.

Aspect 11 provides the sample processing system of aspect 10, wherein the functional group is a carboxyl group.

Aspect 12 provides the sample processing system of any one of aspects 1-11, wherein the sample comprises biomolecules.

Aspect 13 provides the sample processing system of aspect 12, wherein the biomolecules are nucleic acids or proteins.

Aspect 14 provides the sample processing system of any one of aspects 1-13 further comprising:
 a collection component capable of collecting the ferrimagnetic particles in the container, thereby allowing the ferrimagnetic particles to be separated from the sample.

Aspect 15 provides the sample processing system of any one of aspects 1-14, wherein the magnetic assembly further comprises at least one magnetic structure, each magnetic structure comprising a plurality of electromagnets, each of the plurality of electromagnets having an electrically-conductive coil disposed about a centerline that extends toward a center axis of the magnetic structure.

Aspect 16 provides a method for processing a sample, the method comprising:
 providing a container comprising ferrimagnetic particles and a sample; and
 subjecting the container to a changing magnetic field, thereby moving the ferrimagnetic particles in the container and thereby processing the sample.

Aspect 17 provides the method of aspect 16, wherein the processing includes capturing an analyte in the sample.

Aspect 18 provides the method of aspect 17, wherein the ferrimagnetic particles comprise a capture reagent for capturing the analyte in the sample.

Aspect 19 provides the method of aspect 18, wherein the capture reagent is an antibody.

Aspect 20 provides the method of aspect any one of aspects 17-19, wherein the ferrimagnetic particles comprise a functional group for adsorbing the analyte.

Aspect 21 provides the method of aspect 20, wherein the analyte is a nucleic acid and the functional group is a carboxyl group.

Aspect 22 provides the method of any one of aspects 16-21 further comprising:
 collecting, with a collection component, the ferrimagnetic particles: and
 eluting at least a portion of the sample from the container.

Aspect 23 provides the method of any one of aspects 16-22, wherein the processing includes heating or mixing the sample by the movement of the ferrimagnetic particles in the container.

Aspect 24 provides the method of any one of aspect 16-23, wherein the ferrimagnetic particles comprise a ferrite core.

Aspect 25 provides the method of aspect 24, wherein the ferrite core comprises a soft ferrite.

Aspect 26 provides the method of aspect 25, wherein the ferrite core is selected from a group consisting of:
 cobalt ferrite;
 MnZn ferrite; and
 NiZn ferrite.

Aspect 27 provides the method of any one of aspects 16-26, wherein the ferrimagnetic particles further comprise a coating.

Aspect 28 provides the method of aspect 27, wherein the coating is a polymer layer or a silica layer for adjusting the density of the ferrimagnetic particles to be close to the density of a fluid.

Aspect 29 provides the method of any one of aspects 16-28, wherein the sample comprises biomolecules.

Aspect 30 provides the method of aspect 29, wherein the biomolecules are nucleic acids or proteins.

Aspect 31 provides a sample processing system comprising:
 a container configured to receive a sample for processing;
 magnetic particles disposed in the container, the magnetic particles having a maximum field strength in a range of from about 20 emu/g to about 250 emu/g and a remanence in a range of from about 0 emu/g to about 30 emu/g;
 a magnetic assembly disposed about the periphery of the container for creating a changing magnetic field in the container, thereby moving the magnetic particles throughout the container; and
 a control component coupled to the magnetic assembly for controlling the changing magnetic field.

Aspect 32 provides the sample processing system of aspect 31, wherein the magnetic particles comprise ferrimagnetic particles, ferromagnetic particles, paramagnetic particles, superparamagnetic particles, or a mixture thereof.

Aspect 32 provides the sample processing system of aspect 31, wherein the magnetic particles comprise ferrimagnetic particles.

Aspect 34 provides the sample processing system of any one of aspect 31 or 33, wherein the maximum field strength of the magnetic particles in a range of from about 35 emu/g to about 100 emu/g.

Aspect 35 provides the sample processing system of any one of aspects 31-34, wherein the remanence of the magnetic particles is in a range of from about 0 emu/g to about 10 emu/g.

Aspect 36 provides the sample processing system of any one of aspects 31-35, wherein the magnetic particles are porous and a pore size of an individual pore is in a range of from about 5 Å to about 1000 Å.

Aspect 37 provides the sample processing system of any one of aspects 31-36, wherein the magnetic particles are porous and a pore size of an individual pore is in a range of from about 50 Å to about 500 Å.

Aspect 38 provides the sample processing system of any one of aspects 31-37, wherein the magnetic particles comprise a ferrite core.

Aspect 39 provides the sample processing system of any one of aspect 31-38, wherein the ferrite core comprises a soft ferrite.

Aspect 40 provides the sample processing system of any one of aspects 31-39, wherein the ferrite core is selected from a group consisting of $Fe_2TiO_2$, $FeTiO_2$, $MnFe_2O_4$, $NiFe_2O_4$, $MgFe_2O_4$, $Fe_7S$, $Fe_3S_4$, $FeS$, and $FeOOH$.

Aspect 41 provides the sample processing system of any one of aspects 31-40, further comprising:
the sample disposed in the container.

Aspect 42 provides the sample processing system of any one of aspects 31-41, wherein the magnetic particles further comprise a coating.

Aspect 43 provides the sample processing system of aspect 42, wherein the coating comprises $SiO_2$, $TiO_2$, $ZnO_2$, $Al_2O_3$, $CeO_2$, a ceramic, polyacrylic acid, poly(methyl acrylate), polystyrene, divinylbenzene, polyvinylpyrrolidone, polyvinyl alcohol, or a mixture thereof.

Aspect 44 provides the sample processing system of any one of aspects 42 or 43, wherein the coating comprises a capture reagent for capturing an analyte in the sample.

Aspect 45 provides the sample processing system of aspect 44, wherein the capture reagent comprises a thiol group, streptavidin, an amine group, a hydroxyl group, a tosyl group, an epoxy group, an alkyl group, a vinyl group, an aryl group, an enzyme, a protein, a deoxyribonucleic acid, a ribonucleic acid, an immunoglobulin G, a carboxyl group, or a monoclonal antibody.

Aspect 46 provides the sample processing system of aspect 42, wherein the coating comprises an enzyme and the sample comprises a substrate of the enzyme.

Aspect 47 provides the sample processing system of any one of aspects 31-46, wherein the sample comprises biomolecules.

Aspect 48 provides the sample processing system of aspect 47, wherein the biomolecules are nucleic acids or proteins.

Aspect 49 provides the sample processing system of any one of aspects 31-48, further comprising:
a collection component capable of collecting the magnetic particles in the container, thereby allowing the magnetic particles to be separated from the sample.

Aspect 50 provides the sample processing system of any one of aspects 31-49, wherein the magnetic assembly further comprises at least one magnetic structure, each magnetic structure comprising a plurality of electromagnets, each of the plurality of electromagnets having an electrically-conductive coil disposed about a centerline that extends toward a center axis of the magnetic structure.

Aspect 51 provides the sample processing system of any one of aspects 31-50, wherein a permeability of the magnetic particle is sufficient to generate an induced magnetic field in a range of from about 10 emu/g to about 250 emu/g upon exposure to a magnetic field having a strength in a range of from about 700 Oersted to about 800 Oersted.

Aspect 52 provides the sample processing system of any one of aspects 31-51, a permeability of the magnetic particle is sufficient to generate an induced magnetic field in a range of from about 35 emu/g to about 100 emu/g upon exposure to a magnetic field having a strength in a range of from about 700 Oersted to about 800 Oersted.

Aspect 53 provides a method of processing a sample, the method comprising:
providing a container containing magnetic particles and the sample in a solution, the magnetic particles having a ligand on a surface of the particles, wherein the ligand selectively interacts with an analyte of interest in the sample, the magnetic particles having a maximum field strength in a range of from about 20 emu/g to about 250 emu/g and a remanence in a range of from about 0 emu/g to about 30 emu/g;
incubating the solution to allow the analyte of interest to contact the ligand on the surface of the magnetic particles; and
subjecting the container to a magnetic field, thereby allowing the magnetic particles to be separated from the sample.

Aspect 54 provides the method of aspect 53, wherein the ligand is a capture reagent comprising a thiol group, streptavidin, an amine group, a hydroxyl group, a tosyl group, an epoxy group, an alkyl group, a vinyl group, an aryl group, an enzyme, a protein, a deoxyribonucleic acid, a ribonucleic acid, an immunoglobulin G, a carboxyl group, or a monoclonal antibody.

Aspect 55 provides the method of any one of aspects 53 or 54, wherein the analyte is a nucleic acid and the functional group is a carboxyl group.

Aspect 56 provides the method of any one of aspects 53-55, further comprising:
collecting, with a collection component, the magnetic particles; and
eluting at least a portion of the sample from the container.

Aspect 57 provides the method of any one of aspects 53-56, further comprising heating or mixing the sample by the movement of the magnetic particles in the container.

Aspect 58 provides the method of any one of aspects 53-57, wherein the maximum field strength in a range of from about 35 emu/g to about 100 emu/g.

Aspect 59 provides the method of any one of aspects 53-58, wherein the remanence of the magnetic particles is in a range of from about 0 emu/g to about 10 emu/g.

Aspect 60 provides the method of any one of aspects 53-59, wherein the magnetic particles are porous and a pore size of an individual pore is in a range of from about 5 Å to about 1000 Å.

Aspect 61 provides the method of any one of aspects 53-60, wherein the magnetic particles are porous and a pore size of an individual pore is in a range of from about 50 Å to about 500 Å.

Aspect 62 provides the method of any one of aspects 53-61, wherein the magnetic particles comprise a ferrite core.

Aspect 63 provides the method of aspect 62, wherein the ferrite core comprises a soft ferrite.

Aspect 64 provides the method of any one of aspects 61-63, wherein the ferrite core is selected from a group consisting of $Fe_2Ti_2$, $FeTiO_2$, $MnFe_2O_4$, $NiFe_2O_4$, $MgFe_2O_4$, $Fe_7S$, $Fe_3S_4$, FeS, and FeOOH.

Aspect 65 provides the method of any one of aspects 53-64, wherein the magnetic particles further comprise a coating.

Aspect 66 provides the method of aspect 65, wherein the coating comprises $SiO_2$, $TiO_2$, $ZnO_2$, $Al_2O_3$, $CeO_2$, a ceramic, polyacrylic acid, poly(methyl acrylate), polystyrene, divinylbenzene, polyvinylpyrrolidone, polyvinyl alcohol, or a mixture thereof.

Aspect 67 provides the method of any one of aspects 53-66, wherein the analyte of interest comprises biomolecules.

Aspect 68 provides the method of aspect 67, wherein the biomolecules are nucleic acids or proteins.

Aspect 69 provides the method of any one of aspects 53-68, wherein the ligand is an enzyme and the analyte of interest is a substrate of the enzyme.

Aspect 70 provides the method of aspect 69, wherein the enzyme degrades the substrate.

Aspect 71 provides the method of any one of aspects 53-70, wherein the magnetic particle comprise ferrimagnetic particles, ferromagnetic particles, paramagnetic particles, superparamagnetic particles, or a mixture thereof.

Aspect 72 provides the method of any one of aspects 53-71, wherein a permeability of the magnetic particle is sufficient to generate an induced magnetic field in a range of from about 10 emu/g to about 250 emu/g upon exposure to a magnetic field having a strength in a range of from about 700 Oersted to about 800 Oersted.

Aspect 73 provides the method of any one of aspects 53-72, wherein a permeability of the magnetic particle is sufficient to generate an induced magnetic field in a range of from about 35 emu/g to about 100 emu/g upon exposure to a magnetic field having a strength in a range of from about 700 Oersted to about 800 Oersted.

Aspect 74 provides a magnetic particle for processing a sample solution, the magnetic particle comprising:
a magnetic material having a maximum field strength in a range of from about 20 emu/g to about 250 emu/g and a remanence in a range of from about 0 emu/g to about 10 emu/g; and
an outer surface containing a ligand, wherein the ligand interacts with an analyte of interest in the sample solution.

Aspect 75 provides the magnetic particle of aspect 74, wherein the maximum field strength in a range of from about 35 emu/g to about 100 emu/g.

Aspect 76 provides the magnetic particle of any one of aspects 74 or 75, wherein the remanence of the magnetic particle is in a range of from about 0 emu/g to about 10 emu/g.

Aspect 77 provides the magnetic particle of any one of aspects 74-76, wherein the magnetic particle is porous and a pore size of an individual pore is in a range of from about 5 Å to about 1000 Å.

Aspect 78 provides the magnetic particle of any one of aspects 74-77, wherein the magnetic particle is porous and a pore size of an individual pore is in a range of from about 50 Å to about 500 Å.

Aspect 79 provides the magnetic particle of any one of aspects 74-78, wherein the magnetic material comprises a soft ferrite.

Aspect 80 provides the magnetic particle of any one of aspects 74-79, wherein the magnetic material is selected from a group consisting of $Fe_2TiO_2$, $FeTiO_2$, $MnFe_2O_4$, $NiFe_2O_4$, $MgFe_2O_4$, $Fe_7S$, $Fe_3S_4$, FeS, and FeOOH.

Aspect 81 provides the magnetic particle of any one of aspects 74-80, wherein the outer surface comprises $SiO_2$, $TiO_2$, $ZnO_2$, $Al_2O_3$, $CeO_2$, a ceramic, polyacrylic acid, poly(methyl acrylate), polystyrene, divinylbenzene, polyvinylpyrrolidone, polyvinyl alcohol, or a mixture thereof.

Aspect 82 provides the magnetic particle of any one of aspects 74-81, wherein the ligand is a capture reagent comprising a thiol group, streptavidin, an amine group, a hydroxyl group, a tosyl group, an epoxy group, an alkyl group, a vinyl group, an aryl group, an enzyme, a protein, a deoxyribonucleic acid, a ribonucleic acid, an immunoglobulin G, a carboxyl group, or a monoclonal antibody.

Aspect 83 provides the magnetic particle of any one of aspects 74-82, wherein the ligand is an enzyme and the analyte of interest is a substrate of the enzyme.

Aspect 84 provides the magnetic particle of aspect 83, wherein the enzyme degrades the substrate.

Aspect 85 provides the magnetic particle of aspects 74-84, wherein the magnetic material comprises a ferrimagnetic material, a ferromagnetic material, a paramagnetic material, a superparamagnetic material, or a mixture thereof.

Aspect 86 provides the magnetic particle of any one of aspects 74-85, wherein a permeability of the magnetic particle is sufficient to generate an induced magnetic field in a range of from about 10 emu/g to about 250 emu/g upon exposure to a magnetic field having a strength in a range of from about 700 Oersted to about 800 Oersted.

Aspect 87 provides the magnetic particle of any one of aspects 74-86, a permeability of the magnetic particle is sufficient to generate an induced magnetic field in a range of from about 35 emu/g to about 100 emu/g upon exposure to a magnetic field having a strength in a range of from about 700 Oersted to about 800 Oersted.

Aspect 88 provides a magnetic particle for processing a sample solution, the magnetic particle comprising:
a core or inner layer including a magnetic material; and
an outer surface layer including a capture reagent that selectively binds to an analyte of interest in the sample solution,
wherein the magnetic particle has a maximum field strength in a range of from about 20 emu/g to about 250 emu/g and a remanence in a range of from about 0 emu/g to about 10 emu/g.

Aspect 89 provides the magnetic particle of aspect 88, wherein the maximum field strength of the magnetic particle is in a range of from about 35 emu/g to about 100 emu/g.

Aspect 90 provides the magnetic particle of any one of aspects 88 or 89, wherein the remanence in a range of from about 0 emu/g to about 10 emu/g.

Aspect 91 provides the magnetic particle of any one of aspects 88-90, wherein the magnetic particle is porous and a pore size of an individual pore is in a range of from about 5 Å to about 1000 Å.

Aspect 92 provides the magnetic particle of any one of aspects 88-91, wherein the magnetic particle is porous and a pore size of an individual pore is in a range of from about 50 Å to about 500 Å.

Aspect 93 provides the magnetic particle of any one of aspects 88-92, wherein the core or inner layer comprises a soft ferrite.

Aspect 94 provides the magnetic particle of any one of aspects 88-93, wherein the core or inner layer comprises a material selected from a group consisting of $Fe_2TiO_2$, $FeTiO_2$, $MnFe_2O_4$, $NiFe_2O_4$, $MgFe_2O_4$, $Fe_7S_8$, $Fe_3S_4$, FeS, and FeOOH.

Aspect 95 provides the magnetic particle of any one of aspects 88-94, wherein the outer surface layer comprises $SiO_2$, $TiO_2$, $ZnO_2$, $Al_2O_3$, $CeO_2$, a ceramic, polyacrylic acid, poly(methyl acrylate), polystyrene, divinylbenzene, polyvinylpyrrolidone, polyvinyl alcohol, or a mixture thereof.

Aspect 96 provides the magnetic particle of any one of aspects 88-95, wherein the outer surface layer further comprises a capture reagent comprising a thiol group, streptavidin, an amine group, a hydroxyl group, a tosyl group, an epoxy group, an alkyl group, a vinyl group, an aryl group, an enzyme, a protein, a deoxyribonucleic acid, a ribonucleic acid, an immunoglobulin G, a carboxyl group, or a monoclonal antibody.

Aspect 97 provides the magnetic particle of any one of aspects 88-96, wherein the magnetic particle comprises ferrimagnetic materials, ferromagnetic materials, paramagnetic materials, superparamagnetic materials, or a mixture thereof.

Aspect 98 provides the magnetic particle of any one of aspects 88-97, wherein a permeability of the magnetic particle is sufficient to generate an induced magnetic field in a range of from about 10 emu/g to about 250 emu/g upon exposure to a magnetic field having a strength in a range of from about 700 Oersted to about 800 Oersted.

Aspect 99 provides the magnetic particle of any one of aspects 88-98, a permeability of the magnetic particle is sufficient to generate an induced magnetic field in a range of from about 35 emu/g to about 100 emu/g upon exposure to a magnetic field having a strength in a range of from about 700 Oersted to about 800 Oersted.

Aspect 100 provides a method of processing a sample, the method comprising:

providing a magnetic particle having a ligand on a surface of the particle, wherein the ligand selectively interacts with an analyte of interest in the sample, the magnetic particle having a maximum field strength in a range of from about 20 emu/g to about 250 emu/g and a remanence in a range of from about 0 emu/g to about 10 emu/g; and contacting a solution comprising the analyte of interest with the magnetic particle to allow the ligand to interact with the analyte of interest.

Aspect 101 provides the method of aspect 100, further comprising subjecting the magnetic particle to a magnetic field, thereby allowing the magnetic particle to be separated from the solution.

Aspect 102 provides the method of any one of aspects 100 or 101, wherein the ligand is a capture reagent.

Aspect 103 provides the method of aspect 102, wherein the capture reagent is a thiol group, streptavidin, an amine group, a hydroxyl group, a tosyl group, an epoxy group, an alkyl group, a vinyl group, an aryl group, an enzyme, a protein, a deoxyribonucleic acid, a ribonucleic acid, an immunoglobulin G, or a monoclonal antibody.

Aspect 104 provides the method of any one of aspects 100-103, wherein the analyte is a nucleic acid and the functional group is a carboxyl group.

Aspect 105 provides the method of any one of aspects 100-104 wherein the ligand is an enzyme and the analyte of interest is a substrate of the enzyme.

Aspect 106 provides the method of aspect 105, wherein the enzyme degrades the substrate.

Aspect 107 provides the method of any one of aspects 100-106, further comprising:

collecting, with a collection component, the magnetic particle; and eluting at least a portion of the sample.

Aspect 108 provides the method of any one of aspects 100-107, further comprising heating or mixing the sample by the movement of the magnetic particle.

Aspect 109 provides the method of any one of aspects 100-108, wherein the maximum field strength of the magnetic particle is in a range of from about 35 emu/g to about 100 emu/g.

Aspect 110 provides the method of any one of aspects 100-109, wherein the remanence of the magnetic particle is in a range of from about 0 emu/g to about 10 emu/g.

Aspect 111 provides the method of any one of aspects 100-110, wherein the magnetic particle is porous and a pore size of an individual pore is in a range of from about 5 Å to about 1000 Å.

Aspect 112 provides the method of any one of aspects 100-111, wherein the magnetic particle is porous and a pore size of an individual pore is in a range of from about 50 Å to about 500 Å.

Aspect 113 provides the method of any one of aspects 100-112, wherein the magnetic particle comprises a ferrimagnetic core, a ferromagnetic core, a paramagnetic core, or, a superparamagnetic core.

Aspect 114 provides the method of any one of aspects 100-113, wherein the magnetic particle comprise a ferrite core.

Aspect 115 provides the method of aspect 114, wherein the ferrite core comprises a soft ferrite.

Aspect 116 provides the method of any one of aspects 114-115, wherein the ferrite core is selected from a group consisting of $Fe_2TiO_2$, $FeTiO_2$, $MnFe_2O_4$, $NiFe_2O_4$, $MgFe_2O_4$, $Fe_7S_8$, $Fe_3S_4$, FeS, and FeOOH.

Aspect 117 provides the method of any one of aspects 100-116, wherein the magnetic particle further comprises a coating.

Aspect 118 provides the method of aspect 117, wherein the coating comprises $SiO_2$, $TiO_2$, $ZnO_2$, $Al_2O_3$, $CeO_2$, a ceramic, polyacrylic acid, poly(methyl acrylate), polystyrene, divinylbenzene, polyvinylpyrrolidone, polyvinyl alcohol, or a mixture thereof.

Aspect 119 provides the method of any one of aspects 100-118, wherein the analyte of interest comprises biomolecules.

Aspect 120 provides the method of aspect 119, wherein the biomolecules are nucleic acids or proteins.

Aspect 121 provides the method of any one of aspects 100-120, a permeability of the magnetic particle is sufficient to generate an induced magnetic field in a range of from about 10 emu/g to about 250 emu/g upon exposure to a magnetic field having a strength in a range of from about 700 Oersted to about 800 Oersted.

Aspect 122 provides the method of any one of aspects 100-121, a permeability of the magnetic particle is sufficient to generate an induced magnetic field in a range of from about 35 emu/g to about 100 emu/g upon exposure to a magnetic field having a strength in a range of from about 700 Oersted to about 800 Oersted.

What is claimed is:

1. A composition of matter for selectively binding and isolating an analyte of interest in a sample, the composition of matter comprising:

a population of non-aggregated magnetic particles, each magnetic particle having a ferrimagnetic core; and a polymeric coating surrounding the ferrimagnetic core, the coating including a ligand on the surface of the coating, wherein the ligand is chemically configured to selectively bind to the analyte of interest in the sample, the population of magnetic particles having an average diameter of greater than 100 nm, a maximum field strength in a range of from about 20 emu/g to about 70 emu/g, and a remanence in a range of from about 0 emu/g to about 30 emu/g.

2. The composition of matter of claim 1, wherein the ferrimagnetic core of the magnetic particles comprises 100 wt % ferrimagnetic material.

3. The composition of matter of claim 2, wherein the ferrimagnetic material comprises $Fe_2O_3$, $Fe_2TiO_2$, FeTiO, $MnFe_2O_4$, $NiFe_2O_4$, $MgFe_2O_4$, $Fe_7S_8$, $Fe_3S_4$, FeS, or FeOOH, $Fe_3O_4$, or a mixture thereof.

4. The composition of matter of claim 1, wherein the ligand comprises a carboxyl group.

5. The composition of matter of claim 1, wherein the maximum field strength is in a range of from about 35 emu/g to about 60 emu/g.

6. The composition of matter of claim 1, wherein the remanence is in a range of from about 0 emu/g to about 10 emu/g.

7. The composition of claim 1, wherein the coating is free of silica.

8. The composition of matter of claim 1, wherein the ligand is chemically configured to selectively bind to the analyte of interest as a result of a precipitation of the analyte of interest in the sample.

9. The composition of matter of claim 8, wherein the precipitation results from the use of a precipitating reagent.

10. The composition of matter of claim 9, wherein the precipitating reagent comprises a polyalkylene glycol.

11. The composition of matter of claim 10, further comprising the precipitation reagent, present at a concentration suitable to precipitate the analyte of interest in the sample.

12. A kit for processing or analyzing a sample, the kit comprising:
a container;
a population of claim 1.

13. The kit of claim 12, wherein the kit further comprises a reagent that is a precipitating reagent.

14. The kit of claim 13, wherein the precipitating reagent is polyethylene glycol.

15. The kit of claim 14, wherein the polyethylene glycol is disposed in the container.

16. A method of processing a sample, the method comprising:
providing the composition of claim 1
contacting a solution comprising the analyte of interest with the population to allow the ligand to interact with the analyte of interest.

17. The method of claim 16, further comprising subjecting the population to a changing magnetic field generated by a plurality of electromagnets to fully mix the sample.

18. The method of claim 16, wherein the analyte of interest is a nucleic acid.

19. The method of claim 18, further comprising selectively precipitating the nucleic acid of interest using a precipitating reagent comprising polyethylene glycol, wherein the ligand selectively binds to the precipitated nucleic acid.

20. The method of claim 19, wherein the ligand comprises a carboxyl group.

21. The method of claim 16, wherein the maximum field strength is in a range of from about 20 emu/g to about 60 emu/g.

22. The method of claim 21, wherein the remanence is in a range of from about 0 emu/g to about 10 emu/g.

23. The method of claim 22, wherein the magnetic particles comprises 100 wt % ferrimagnetic material.

24. The method of claim 23, wherein the ferrimagnetic material comprises $Fe_2O_3$, $Fe_2TiO_2$, FeTiO, $MnFe_2O_4$, $NiFe_2O_4$, $MgFe_2O_4$, $Fe_7S_8$, $Fe_3S_4$, FeS, or FeOOH, $Fe_3O_4$, or a mixture thereof.

* * * * *